United States Patent
Liu et al.

(10) Patent No.: US 11,583,584 B1
(45) Date of Patent: *Feb. 21, 2023

(54) STABLE PROTEIN COMPOSITIONS AND METHODS OF THEIR USE

(71) Applicant: Coherus Biosciences, Inc., Redwood City, CA (US)

(72) Inventors: Jun Liu, Pacifica, CA (US); Mark Manning, Johnstown, CO (US); Isaias Prado, Oxnard, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 15/337,845

(22) Filed: Oct. 28, 2016

Related U.S. Application Data

(60) Provisional application No. 62/413,226, filed on Oct. 26, 2016, provisional application No. 62/357,466, filed on Jul. 1, 2016, provisional application No. 62/247,348, filed on Oct. 28, 2015.

(51) Int. Cl.
| | | |
|---|---|---|
| *A61K 39/395* | (2006.01) | |
| *A61K 9/00* | (2006.01) | |
| *A61K 47/40* | (2006.01) | |
| *A61K 47/42* | (2017.01) | |
| *A61K 47/18* | (2017.01) | |
| *A61K 47/34* | (2017.01) | |
| *A61K 47/02* | (2006.01) | |
| *A61K 47/12* | (2006.01) | |

(52) U.S. Cl.
CPC ...... *A61K 39/39591* (2013.01); *A61K 9/0019* (2013.01); *A61K 39/3955* (2013.01); *A61K 47/02* (2013.01); *A61K 47/12* (2013.01); *A61K 47/183* (2013.01); *A61K 47/34* (2013.01); *A61K 47/40* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 5,376,632 A * | 12/1994 | Konings | A61K 38/1816 514/58 |
| 6,090,382 A | 7/2000 | Salfeld | |
| 6,258,562 B1 | 7/2001 | Salfeld | |
| 6,509,015 B1 | 1/2003 | Salfeld | |
| 8,664,945 B2 | 3/2014 | Laville | |
| 8,916,157 B2 * | 12/2014 | Krause | A61K 9/19 424/158.1 |
| 9,724,415 B2 * | 8/2017 | Manning | A61K 47/12 |
| 9,731,008 B2 * | 8/2017 | Manning | A61K 47/12 |
| 9,731,009 B2 * | 8/2017 | Manning | A61K 47/12 |
| 9,737,600 B2 * | 8/2017 | Manning | A61K 47/12 |
| 9,770,507 B2 * | 9/2017 | Manning | A61K 47/12 |
| 9,782,480 B2 * | 10/2017 | Manning | A61K 47/12 |

OTHER PUBLICATIONS

Humira insert, Abbot Lab, 2002, p. 1-34.*

* cited by examiner

*Primary Examiner* — Yunsoo Kim
(74) *Attorney, Agent, or Firm* — Fish & Richardson P.C.

(57) ABSTRACT

The present invention is directed to compositions and methods for stabilizing a protein without a surfactant. The present invention is further directed to compositions comprising a protein and at least one excipient selected from the group consisting of hindered amines, anionic aromatics, functionalized amino acids, oligopeptides, low molecular weight aliphatic polyacids, zwitterions, phospholipids, cyclodextrins, polyethylene glycols, gelatins, urea, ethanol, glycerin, dextran, xanthan gum, 2-(2-ethoxyethoxy)ethanol, hydroxypropyl cellulose, propylene glycol, a short-chain organic acid, deoxycholate, sodium nitrate, sodium sulfate, proline and lysine.

44 Claims, 3 Drawing Sheets

36: 0.05% Caproic acid, 0.75% HPβCD, 0.75% PEG 300
27: 1% Caproic acid, 10% PEG 2000
1: 25 mM HPβCD
6: 0.5% HPC SIC Studies ($B_{22}$ Values)

STABLE PROTEIN COMPOSITIONS AND METHODS OF THEIR USE

CROSS-REFERENCE TO RELATED APPLICATION

This application claims priority to U.S. Provisional Patent Application Ser. No. 62/247,348, filed on Oct. 28, 2015, U.S. Provisional Patent Application Ser. No. 62/357,466, filed on Jul. 1, 2016, and U.S. Provisional Patent Application Ser. No. 62/413,226, filed on Oct. 26, 2016.

BACKGROUND OF THE INVENTION

Auto-immune diseases affect nearly 24 million people in the United States (roughly 8% of the population) alone making it one of the most prevalent diseases. By comparison, heart disease affects 22 million and cancer 9 million. Many auto-immune diseases are correlated with elevated levels of a naturally occurring protein in the body known as tumor necrosis factor ("TNFα"). TNFα is a cytokine capable of inducing fever, cell death and inflammation among other illnesses. TNFα works by binding to and activating cell surface receptors which lead to the activation of genes involved in inflammation.

Adalimumab is an anti-inflammatory drug targeted to inhibiting TNFα from binding to these cell surface receptors. Adalimumab is the first fully human monoclonal antibody approved by the United States Food and Drug Administration (FDA) and is sold by AbbVie Biotechnology LTD under the trademark Humira® (Humira is a registered trademark of AbbVie Biotechnology LTD). Humira® has been approved by the FDA for several auto-immune diseases including rheumatoid arthritis, psoriatic arthritis, ankylosing spondylitis, Crohn's disease, ulcerative colitis, moderate to severe chronic psoriasis and juvenile idiopathic arthritis.

Pharmaceutical formulations need to be stable to allow for storage and efficacy of the active ingredient drug product. Excipients are frequently added to formulations to increase stability. However, interactions between compounds and the drug product are complex and unpredictable. Especially for large complex molecules like antibodies. While some excipients are known to stabilize formulations in one aspect, they may destabilize them in another.

For example, the surfactant polysorbate 80 is a non-ionic excipient prevalently known to increase physical stability of proteins upon exposure to hydrophobic-hydrophilic interfaces such as air-water and ice-water. However, as shown herein, polysorbate 80 decreases colloidal stability of adalimumab. All formulations of adalimumab drug products (Humira® and Amjevita™) contain polysorbate 80. New formulations of adalimumab without surfactants can improve product stability.

Thus, there is still need for new liquid formulations of pharmaceutical proteins (e.g. adalimumab) that are stable and allow for product storage without substantial loss in efficacy.

SUMMARY OF THE INVENTION

The present invention is directed to surfactant free protein compositions that are stable as a result of at least one other excipient. In a preferred embodiment the compositions of the invention are further free of polyols.

DETAILED DESCRIPTION OF THE INVENTION

Figure 1:
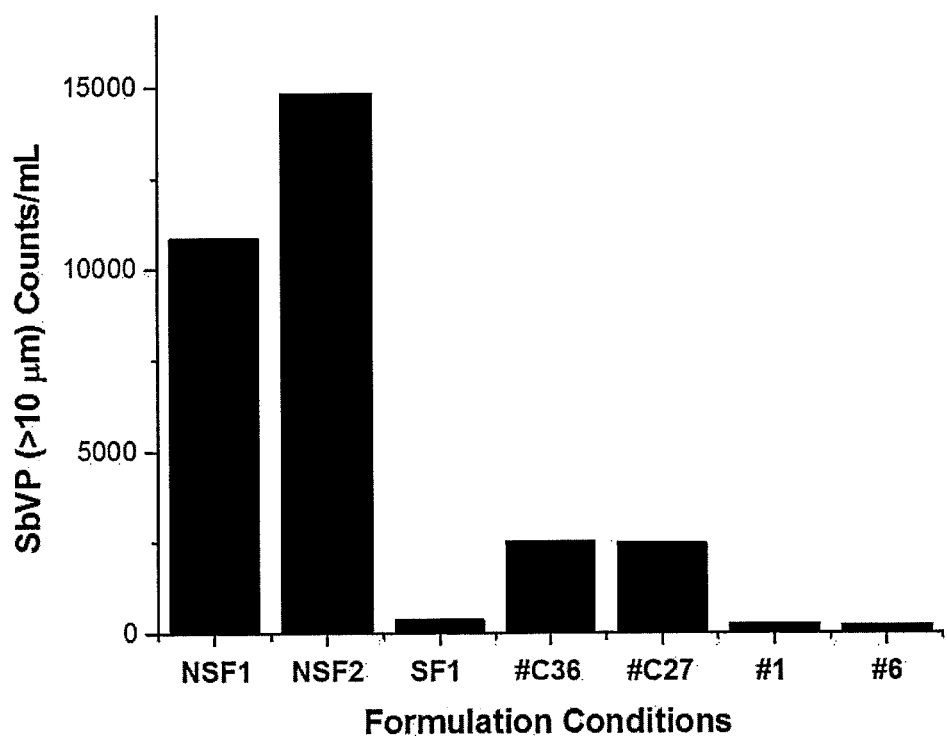
FIG. 1. Sub-visible particle content of surfactant free formulations.

The present invention is directed to stable protein compositions comprising non-surfactant excipients that prevent interaction of the protein with the gas-solution and/or container/solution interface as well as provide a reduction or elimination of contact between the proteins. In a preferred embodiment compositions of the invention are free of surfactants. In a more preferred embodiment the compositions of the invention are further free of polyols.

Not wishing to be held to a particular theory, excipients, suitable for the present invention are of a particular size range; this size range is critical in reducing or preventing contact between proteins and between proteins and the gas/solution or container/solution interface while not increasing protein aggregation.

As used herein the term "protein" refers to a chain of amino acids capable of forming a tertiary structure. Both naturally-occurring proteins, non-naturally-occurring proteins and other polypeptides are included in the present invention. A preferred protein for use in the present invention is an antibody.

As used herein, the term "antibody" or "antibodies" refers to immunoglobulin molecules comprised of four polypeptide chains, two heavy (H) chains and two light (L) chains connected by disulfide bonds. Antibodies capable of being utilized in the present invention include but are not limited to recombinant human antibodies including human monoclonal antibodies and 'fully' human monoclonal antibodies. Examples of antibodies which may be utilized in the methods and compositions of the present invention include tumor necrosis factor (TNF)-α antibodies (also referred to as anti-TNFα antibodies). TNFα antibodies which may be utilized in the invention include adalimumab (adalimumab is sold under the trademark Humira® and is described in further detail in U.S. Pat. Nos. 6,090,382; 6,258,562; 6,509,015; and 8,664,945, each of which is incorporated herein by reference in its entirety), adalimumab-atto (adalimumab-atto is given the trademark Amjevita™), infliximab (infliximab is sold under the trademark REMICADE®; Remicade is a registered trademark of Janssen Biotech, Inc.), certolizumab pegol (pegol is sold under the trademark CIMZIA®; Cimzia is a registered trademark of UCB Pharma, SA) and golimumab (golimumab is sold under the trademark SIMPONI®; Simponi is a registered trademark of Johnson & Johnson). Other antibodies that may be utilized in the methods of this invention include natalizumab (natalizumab is sold under the trademark TYSABRI®; Tysabri is a registered trademark of Biogen Idec MA, Inc.), ranibizumab (ranibizumab is sold under the trademark LUCENTIS®; Lucentis is a registered trademark of Genentech, Inc.), bevicizumab (bevicizumab is sold under the trademark AVASTIN®; Avastin is a registered trademark of Genentech, Inc.), rituximab (rituximab is sold under the trademark RITUXAN®; Rituxan is a registered trademark of Biogen Idec, Inc.), eculizumab (eculizumab is sold under the trademark SOLIRIS®; Soliris is a registered trademark of Alexion Pharmaceuticals, Inc.), ustekinumab (ustekinumab is sold under the trademark STELARA®; Stelara is a registered trademark of Johnson & Johnson, Inc.), denosumab (denosumab is sold under the trademarks PROLIA®; Prolia is a registered trademark of Amgen, Inc. and XGEVA®; Xgeva is a registered trademark of Amgen, Inc.), tocilizumab (tocilizumab is sold under the trademark ACTEMRA®; Actemra is a registered trademark of Chugai Seiyaku Kabushiki Kaisha Corp.), ipilimumab (ipilimumab is sold under the trademark YERVOY®; Yervoy is a registered trademark of Bristol-Myers Squibb Comp.), omalizumab (omalizumab is sold under the trademark XOLAIR®; Xolair is a registered trademark of Novartis AG), ramucirumab (ramucirumab is sold under the trademark CYRAMZA®; Cyramza is a registered trademark of ImClone LLC), vedolizumab (vedolizumab is sold under the trademark ENTYVIO®; Entyvio is a registered trademark of Millennium Pharmaceuticals, Inc.), belimumab (belimumab is sold under the trademark BENLYSTA®; Benlysta is a registered trademark of GlaxoSmithKline Intellectual Property Limited), epratuzumab, nivolumab, secukinumab, gevokizumab and biosimilars thereof.

The term "biosimilar" or "biosimilars," as used herein, refers to a biological product designed to have active properties similar to an FDA-licensed biological product. Further, these terms refer to a biologic product that is highly similar to a FDA-licensed biological product (the "reference product"), notwithstanding minor differences in clinically inactive components, and there are no clinically meaningful differences between the biological product and the reference product in terms of the safety, purity, and potency of the product.

The term "adalimumab" is synonymous with the active pharmaceutical ingredient in Humira® as well as protein considered or intended as biosimilar or bio-better variants thereof. Adalimumab is a recombinant human IgG1 monoclonal antibody specific for human TNF. Adalimumab is also known as D2E7. Adalimumab has two light chains, each with a molecular weight of approximately 24 kilodaltons (kDa) and two IgG1 heavy chains each with a molecular weight of approximately 49 kDa. Each light chain consists of 214 amino acid residues and each heavy chain consists of 451 amino acid residues. Thus, adalimumab consists of 1330 amino acids and has a total molecular weight of approximately 148 kDa. The term adalimumab is also intended to encompass so-called bio-similar or bio-better variants of the adalimumab protein used in commercially available Humira®. For example, a variant of commercial Humira® may be acceptable to the FDA when it has essentially the same pharmacological effects as commercially available Humira®, even though it may exhibit certain physical properties, such as glycosylation profile, that may be similar if not identical to Humira®.

For the purposes of the present application, the term "adalimumab" also encompasses adalimumab with minor modifications in the amino acid structure (including deletions, additions, and/or substitutions of amino acids) or in the glycosylation properties, which do not significantly affect the function of the polypeptide. The term "adalimumab" encompasses all forms and formulations of Humira® and Amjevita™, including but not limited to concentrated formulations, injectable ready-to-use formulations; formulations reconstituted with water, alcohol, and/or other ingredients, and others.

Known formulations of adalimumab include those of Humira®, Amjevita™, and formulations disclosed in the literature. For example, Humira is available in 50 mg/mL and 100 mg/mL concentrations of adalimumab.

For the Humira 50 mg/mL adalimumab formulations each 0.8 mL composition of Humira® contains adalimumab 40 mg, citric acid monohydrate 1.04 mg, dibasic sodium phosphate dihydrate 1.22 mg, mannitol 9.6 mg, monobasic sodium phosphate dihydrate 0.69 mg, polysorbate 80 0.8 mg, sodium chloride 4.93 mg, sodium citrate 0.24 mg and Water for Injection, USP. Sodium hydroxide is added as necessary to adjust pH. In alternate units, Humira® contains adalimumab 50 mg/mL, sodium chloride 105 mM, sodium phosphate 14.1 mM, sodium citrate 7.2 mM, mannitol 1.2%, polysorbate 80 0.1%, at pH 5.2.

For the Humira 100 mg/mL adalimumab formulations, each 0.4 mL of HUMIRA contains adalimumab 40 mg, mannitol 16.8 mg, polysorbate 80 0.4 mg, and Water for Injection, USP. In alternative units, this Humira formulation is 100 mg/mL adalimuamb, 231 mM Mannitol, 0.1% PS80 at pH 5.2.

The Amjevita™ package insert discloses that 40 mg/0.8 mL prefilled syringe or prefilled autoinjector delivers 0.8 mL (40 mg) of drug product and that each 0.8 mL of Amjevita™ is formulated with glacial acetic acid (0.48 mg), polysorbate 80 (0.8 mg), sodium hydroxide for pH adjustment, sucrose (72 mg), and Water for Injection, USP, pH 5.2. The Amjevita™ package insert also states that each 20 mg/0.4 mL prefilled syringe delivers 0.4 mL (20 mg) of drug product amd each 0.4 mL of Amjevita™ is formulated with glacial acetic acid (0.24 mg), polysorbate 80 (0.4 mg), sodium hydroxide for pH adjustment, sucrose (36 mg), and Water for Injection, USP, pH 5.2.

An alternative adalimumab composition contains adalimumab 50 mg/mL, sodium chloride 44 mM, glycine 160 mM, histidine 30 mM, polysorbate 80 0.1%, at pH 5.3.

Adalimumab may be at a concentration from about 20 to about 1,000 milligrams per milliliter ("mg/mL"), preferably from about 50 to about 120 mg/mL and more preferably at about 50 mg/mL or 100 mg/mL.

As used herein, the term "excipient" or "excipients" refers to an inactive ingredient of the pharmaceutical compositions of the invention.

As used herein, the term "substantially free" and "essentially free," used interchangeably, mean that either no substance is present or only minimal, trace amounts of the substance are present which do not have any substantial impact on the properties of the composition. In a particular embodiment, a composition is substantially free of a substance if at least 95%, 96%, 97%, 98%, 99%, 99.5%, or 99.8% of the substance has been removed. In another embodiment, substantially free means the substance is not present in amount sufficient to perform a function in composition for which a skilled artisan would use the substance. If reference is made to no amount of a substance, it should be understood as "no detectable amount."

As used herein, the term "short chain organic acids" refers to organic acids with an aliphatic tail from 2 to 13 carbon atoms. Short chain organic acids include, but are not limited to, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, caproleic acid, lauroleic acid and salts thereof and combinations thereof.

As used herein, the term "hindered amine" refers to a small molecule containing at least one bulky or sterically hindered group, consistent with the examples below. Hindered amines can be used in the free base form, in the protonated form, or a combination of the two. In protonated forms, the hindered amines can be associated with an anionic counterion such as chloride, hydroxide, bromide, iodide, fluoride, acetate, formate, phosphate, sulfate, or carboxylate. Hindered amine compounds useful as excipient compounds can contain secondary amine, tertiary amine, quaternary ammonium, pyridinium, pyrrolidone, pyrrolidine, piperidine, morpholine, or guanidinium groups, such that the excipient compound has a cationic charge in aqueous solution at neutral pH. The hindered amine compounds also contain at least one bulky or sterically hindered group, such as cyclic aromatic, cycloaliphatic, cyclohexyl, or alkyl groups. In embodiments, the sterically hindered group can itself be an amine group such as a dialkylamine, trialkylamine, guanidinium, pyridinium, or quaternary ammonium group. Hindered amines suitable for the present invention include, but are not limited to, imidazole, 1-methylimidazole, 4-methylimidazole, 1-hexyl-3-methylimidazolium chloride, histamine, 4-methylhistamine, alpha-methylhistamine, betahistine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, anserine, dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane,tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, dicyandiamide-aminomethanephosphonic acid adducts, aminophylline, 3-isobutyl-1-methylxanthine, paraxanthine pentoxifylline and combinations thereof.

As used herein the term "anionic aromatics" refers to compounds that contain an aromatic functional group such as phenyl, benzyl, aryl, alkylbenzyl, hydroxybenzyl, phenolic, hydroxyaryl, heteroaromatic group, or a fused aromatic group. The anionic aromatic excipient compounds also can contain an anionic functional group such as carboxylate, oxide, phenoxide, sulfonate, sulfate, phosphonate, phosphate, or sulfide. While the anionic aromatic excipients might be described as an acid, a sodium salt, or other, it is understood that the excipient can be used in a variety of salt forms. Anionic aromatics suitable for use in the present invention, include but are not limited to, salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and salts thereof and combinations thereof.

As used herein, the term "functionalized amino acids" refers to molecules ("amino acid precursors") that can be hydrolyzed or metabolized to yield amino acids. In embodiments, the functionalized amino acids can contain an aromatic functional group such as phenyl, benzyl, aryl, alkylbenzyl, hydroxybenzyl, hydroxyaryl, heteroaromatic group, or a fused aromatic group. In embodiments, the functionalized amino acid compounds can contain esterified amino acids, such as methyl, ethyl, propyl, butyl, benzyl, cycloalkyl, glyceryl, hydroxyethyl, hydroxypropyl, PEG, and PPG esters. In embodiments, the functionalized amino acid compound is a charged ionic compound in aqueous solution at neutral pH. For example, a single amino acid can be derivatized by forming an ester, like an acetate or a benzoate, and the hydrolysis products would be acetic acid or benzoic acid, both natural materials, plus the amino acid. Functionalized amino acids suitable for use in the present invention include, but are not limited to, of arginine ethyl ester, arginine methyl ester, arginine hydroxyethyl ester, and arginine hydroxypropyl ester and combinations thereof.

As used herein, the term "oligopeptides" refers to peptides with from 2 to 10 amino acids. In certain embodiments, the oligopeptide has a structure with a charged section and a bulky section. The oligopeptide can be bi-functional, for example a cationic amino acid coupled to a non-polar one, or an anionic one coupled to a non-polar one. In embodiments, the oligopeptides consist of from 2 to 5 amino acids. In embodiments, the oligopeptides have a net cationic charge. In embodiments, the oligopeptide can have an alternating structure such as an ABA repeating pattern. In embodiments, the oligopeptide can contain both anionic and cationic amino acids, for example, Arg-Glu.

As used herein, the term "low molecular weight aliphatic polyacids" refers to organic aliphatic polyacids having a molecular weight<about 1500, and having at least two acidic groups, where an acidic group is understood to be a proton-donating moiety. Non-limiting examples of acidic groups include carboxylate, phosphonate, phosphate, sulfonate, sulfate, nitrate, and nitrite groups. Acidic groups on the low molecular weight aliphatic polyacid can be in the anionic salt form such as carboxylate, phosphonate, phosphate, sulfonate, sulfate, nitrate, and nitrite; their counterions can be sodium, potassium, lithium, and ammonium. Anionic salts of the low molecular weight aliphatic polyacids may contain a counterion selected from sodium, lithium, potassium and ammonium. As used herein, the low molecular weight aliphatic polyacid can also be an alpha hydroxy acid, where there is a hydroxyl group adjacent to a first acidic group. In embodiments, the low molecular weight aliphatic polyacid is an oligomeric form that bears more than two acidic groups. Low molecular weight aliphatic polyacids suitable for the present invention include, but are not limited to, maleic acid, tartaric acid, glutaric acid, malonic acid, citric acid, ethylenediaminetetraacetic acid (EDTA), aspartic acid, glutamic acid, alendronic acid, etidronic acid, glycolic acid, lactic acid, gluconic acid, polyacrylic acid, polyphosphates, polypeptides and salts thereof.

As used herein, the term "zwitterions" refers to neutral molecules that simultaneously have both positive and negative charges. Common zwitterions include amino acids.

Cyclodextrins suitable for use in the present invention include, but are not limited to, alpha-, beta- and gamma-cyclodextrins, αCD, βCD, and γCD, respectively. Preferred cyclodextrins include derivatized cyclodextrins. Derivatized cyclodextrin many contain a range of derivatives attached through the three available hydroxyl groups on each glucopyranose unit. The terms substituted and derivatized are used to refer to hydroxyl groups that have been replace with another group. Up to 18 (αCD), 21 (βCD), or 24 (γCD) degrees of substitution may be achieved, with numerous positional and regioisomers possible. Examples of derivatized cyclodextrins include, but are not limited to, methylbeta-cyclodextrins ("MβCD"); randomly methylated-beta-cyclodextrin ("RMβCD"); Sulfobutylether-beta-cyclodextrins ("SBEβCD") (e.g. Captisol® which has six to seven sulfobutyl ether groups per cyclodextrin molecule); hydroxypropyl-beta-cyclodextrins ("HPβCD") (e.g. Cavasol® W7 HP HPβCD, Cavitron™ W7 HP7 HPβCD, and Cavitron™ W7 HP5 HPβCD) including 2-hydroxypropyl-beta-cyclodextrin; hydroxypropyl-gamma-cyclodextrins ("HPγCD"), including 2-hydroxypropyl-gamma-cyclodextrins. A preferred cyclodextrin is hydroxypropyl-beta-cyclodextrin ("HPβCD").

The hydroxypropyl beta cyclodextrin is a partially substituted poly (hydroxypropyl) ether beta cyclodextrin. In one embodiment, the number of hydroxypropyl groups per anhydroglucose unit, expressed as molar substitution is no less than (NLT) 0.40 to no more than (NMT) 1.50. Put otherwise, the average substitution of HPβCD is about 0.4 to about 1.50. In another embodiment, the average substitution of HPβCD is at least about 0.61. HPβCD with higher degree of substitution provide better protection for proteins.

In another embodiment, the average substitution of HPβCD is about 0.4, about 0.41, about 0.42, about 0.43, about 0.44, about 0.45, about 0.46, about 0.47, about 0.48, about 0.49, about 0.5, about 0.51, about 0.52, about 0.53, about 0.54, about 0.55, about 0.56, about 0.57, about 0.58, about 0.59, about 0.6, about 0.61, about 0.62, about 0.63, about 0.64, about 0.65, about 0.66, about 0.67, about 0.68, about 0.69, about 0.7, about 0.71, about 0.72, about 0.73, about 0.74, about 0.75, about 0.76, about 0.77, about 0.78, about 0.79, about 0.8, about 0.81, about 0.82, about 0.83, about 0.84, about 0.85, about 0.86, about 0.87, about 0.88, about 0.89, about 0.9, about 0.91, about 0.92, about 0.93, about 0.94, about 0.95, about 0.96, about 0.97, about 0.98, about 0.99, about 1, about 1.01, about 1.02, about 1.03, about 1.04, about 1.05, about 1.06, about 1.07, about 1.08, about 1.09, about 1.1, about 1.11, about 1.12, about 1.13, about 1.14, about 1.15, about 1.16, about 1.17, about 1.18, about 1.19, about 1.2, about 1.21, about 1.22, about 1.23, about 1.24, about 1.25, about 1.26, about 1.27, about 1.28, about 1.29, about 1.3, about 1.31, about 1.32, about 1.33, about 1.34, about 1.35, about 1.36, about 1.37, about 1.38, about 1.39, about 1.4, about 1.41, about 1.42, about 1.43, about 1.44, about 1.45, about 1.46, about 1.47, about 1.48, about 1.49, about 1.5, about 1.51, about 1.52, about 1.53, about 1.54, about 1.55, about 1.56, about 1.57, about 1.58, about 1.59, about 1.6, about 1.61, about 1.62, about 1.63, about 1.64, about 1.65, about 1.66, about 1.67, about 1.68, about 1.69, about 1.7, about 1.71, about 1.72, about 1.73, about 1.74, about 1.75, about 1.76, about 1.77, about 1.78, about 1.79, about 1.8, about 1.81, about 1.82, about 1.83, about 1.84, about 1.85, about 1.86, about 1.87, about 1.88, about 1.89, about 1.9, about 1.91, about 1.92, about 1.93, about 1.94, about 1.95, about 1.96, about 1.97, about 1.98, about 1.99, about 2, about 2.01, about 2.02, about 2.03, about 2.04, about 2.05, about 2.06, about 2.07, about 2.08, about 2.09, about 2.1, about 2.11, about 2.12, about 2.13, about 2.14, about 2.15, about 2.16, about 2.17, about 2.18, about 2.19, about 2.2, about 2.21, about 2.22, about 2.23, about 2.24, about 2.25, about 2.26, about 2.27, about 2.28, about 2.29, about 2.3, about 2.31, about 2.32, about 2.33, about 2.34, about 2.35, about 2.36, about 2.37, about 2.38, about 2.39, about 2.4, about 2.41, about 2.42, about 2.43, about 2.44, about 2.45, about 2.46, about 2.47, about 2.48, about 2.49, about 2.5, about 2.51, about 2.52, about 2.53, about 2.54, about 2.55, about 2.56, about 2.57, about 2.58, about 2.59, about 2.6, about 2.61, about 2.62, about 2.63, about 2.64, about 2.65, about 2.66, about 2.67, about 2.68, about 2.69, about 2.7, about 2.71, about 2.72, about 2.73, about 2.74, about 2.75, about 2.76, about 2.77, about 2.78, about 2.79, about 2.8, about 2.81, about 2.82, about 2.83, about 2.84, about 2.85, about 2.86, about 2.87, about 2.88, about 2.89, about 2.9, about 2.91, about 2.92, about 2.93, about 2.94, about 2.95, about 2.96, about 2.97, about 2.98, about 2.99, or about 3.

The degree of substitution can be ascertained using conventional methods such as NMR and HPLC In one embodiment, the cyclodextrin meets USP and/or EP requirements.

In a another embodiment the amount of HPβCD is from about 0.1% to about 50% w/v, about 3% to about 21% w/v, about 6% to about 12% w/v, about greater than 10 mM, from about greater than 10 mM to about 150 mM, from about 25 mM to about 100 mM, from about 50 mM to about 75 mM, about 25 mM, about 50 mM, about 70 mM or about 75 mM.

In a further embodiment, the amount of HPβCD is about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, about 100 mM, about 101 mM, about 102 mM, about 103 mM, about 104 mM, about 105 mM, about 106 mM, about 107 mM, about 108 mM, about 109 mM, about 110 mM, about 111 mM, about 112 mM, about 113 mM, about 114 mM, about 115 mM, about 116 mM, about 117 mM, about 118 mM, about 119 mM, about 120 mM, about 121 mM, about 122 mM, about 123 mM, about 124 mM, about 125 mM, about 126 mM, about 127 mM, about 128 mM, about 129 mM, about 130 mM, about 131 mM, about 132 mM, about 133 mM, about 134 mM, about 135 mM, about 136 mM, about 137 mM, about 138 mM, about 139 mM, about 140 mM, about 141 mM, about 142 mM, about 143 mM, about 144 mM, about 145 mM, about 146 mM, about 147 mM, about 148 mM, about 149 mM, about 150 mM, about 151 mM, about 152 mM, about 153 mM, about 154 mM, about 155 mM, about 156 mM, about 157 mM, about 158 mM, about 159 mM, about 160 mM, about 161 mM, about 162 mM, about 163 mM, about 164 mM, about 165 mM, about 166 mM, about 167 mM, about 168 mM, about 169 mM, about 170 mM, about 171 mM, about 172 mM, about 173 mM, about 174 mM, about 175 mM, about 176 mM, about 177 mM, about 178 mM, about 179 mM, about 180 mM, about 181 mM, about 182 mM, about 183 mM, about 184 mM, about 185 mM, about 186 mM, about 187 mM, about 188 mM, about 189 mM, about 190 mM, about 191 mM, about 192 mM, about 193 mM, about 194 mM, about 195 mM, about 196 mM, about 197 mM, about 198 mM, about 199 mM, or about 200 mM.

Cyclodextrins have pharmaceutical utility as stabilizers and solubilizers which prevent protein aggregation. Cyclodextrins non-covalently complex with proteins through association of the cyclodextrin hydrophobic cavity with hydrophobic amino acids (e.g. Phe, Tyr, Trp) on the protein surface. Unlike non-ionic surfactants, cyclodextrins do not form micelles and do not significantly reduce surface tension at liquid-air interfaces. Additionally, cyclodextrins are effective at higher concentration than non-ionic surfactants. Thus, the stabilizing effect of cyclodextrins on proteins, and protein formulations, is understood to be a result of direct interaction with the protein rather than a surface effect.

Cellulose derivatives suitable for use in the present invention include those known by one of skill in the art to be suitable for pharmaceutical use. Such celluloses include but are not limited to, hydroxypropyl cellulose ("HPC"). In a preferred embodiment the amount of HPC is about 0.01% to about 20% w/v, about 0.05% to about 10% w/v, about 0.1% to about 5% w/v, about 0.2% to about 2% w/v, about 0.1% to about 5% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, or about 1% w/v.

Polyethylene glycols suitable for use in the present invention include, but are not limited to, polyethylene glycols with a molecular mass from about 100 daltons to about 100 kilodaltons, preferably from about 200 daltons to about 20 kilodaltons. Examples of polyethylene glycols suitable for the present invention include, but are not limited to, PEG 300, PEG 400, PEG 3350 and combinations thereof. In a preferred embodiment, the amount of polyethylene glycol is from about 0.1% w/v to about 50% w/v, more preferably from about 0.75% w/v to about 15% w/v and most preferably from about 1% to about 2% w/v.

As used herein, the term "stable" means a protein is physically stable, chemically stable, or both. With respect to storage, and long-term storage, is understood to mean that a protein contained in the pharmaceutical compositions does not lose more than 20%, 15%, 10%, or 5% of its activity relative to activity of the composition at the beginning of storage. The term also should be understood to mean that the protein compositions are at least comparable to, and alternatively better than commercially available protein compositions, in terms of their ability to resist formation of particulates, aggregates, and/or fragments during long term storage.

Stability of a protein in an aqueous formulation may also be defined as the percentage of monomer, aggregate, or fragment, or combinations thereof, of the protein in the formulation. A protein "retains its physical stability" in a formulation if it shows substantially no signs of aggregation, precipitation and/or denaturation upon visual examination of color and/or clarity, or as measured by UV light scattering or by size exclusion chromatography. In one aspect of the invention, a stable aqueous formulation is a formulation having less than about 10%, or less than about 5% of the protein being present as aggregate in the formulation.

In one aspect of the invention, the composition comprising a protein and an excipient of the present invention is stable under conditions (a period of time at a temperature) including, but not limited to: at least 1 week at 40° C., at least 6-10 days at 25-30° C., at least 1-2 weeks at 25-40° C., at least 4 weeks at 25° C., at least 9 weeks at 25° C., at least 13 weeks at 25° C., at least 13 weeks at 5° C., at least 26 weeks at 5° C., at least 52 weeks at 0-8° C., at least 96 weeks at 0-8° C., and least 104 weeks at 0-8° C.

Various analytical techniques for measuring protein stability, including techniques for measuring the type and degree of particulates that may be present in protein formulations, are available in the art and are reviewed in Peptide and Protein Drug Delivery, 247-301 (Vincent Lee ed., *Marcel Dekker*, New York, N.Y., 1991) and Jones, 1993 *Adv. Drug Delivery Rev.* 10: 29-90, for examples. Stability can be measured at a selected temperature for a selected time period as exemplified by the provided examples.

As used herein, the term "surfactant" refers to compounds such as polyoxyethylensorbitan fatty acid esters (e.g. polysorbates, Tween®), polyoxyethylene alkyl ethers (e.g. Brij®), alkylphenylpolyoxyethylene ethers (e.g. Triton-X®), polyoxyethylene-polyoxypropylene copolymers (e.g. poloxamers, Pluronic®), and sodium dodecyl sulfate. Surfactants are characterized by the ability to form micelles, preferentially accumulate at liquid-air interfaces, and disrupt and/or displace protein at liquid-air interfaces. As result, surfactants significantly reducing the surface tension of liquids.

Techniques for determining if a substance forms micelles include surface tension measurements and extrinsic fluorescence spectroscopy. Surface tension measurement techniques include tensiometry and pendant drop methods. Extrinsic fluorescence spectroscopy measures the changes in the emission spectrum of a dye, indicating the formation of the micelle as the local environment around dye changes from hydrophilic to hydrophobic. Excipients of the present invention (e.g. HPβCD) do not form micelles at the concentrations used herein.

As used herein, the terms "treating," "treat" or "treatment" refer to reversing, alleviating or slowing the progress of the disease, disorder, or condition to which such terms apply, or one or more symptoms of such disease, disorder, or condition.

As used herein, the term "pharmaceutically effective amount" refers to an amount sufficient to effect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, a "pharmaceutically effective amount" will depend upon the context in which it is being administered. A pharmaceutically effective amount may be administered in one or more prophylactic or therapeutic administrations.

The term "subject" includes mammals. Mammals include but are not limited to humans. The terms "patient" and "subject" are used interchangeably.

As used herein, all numerical values relating to amounts, weights, and the like, that are defined as "about" each particular value is plus or minus 10%. For example, the phrase "about 10% w/w" is to be understood as "9% to 11% w/w." Therefore, amounts within 10% of the claimed value are encompassed by the scope of the claims.

In one embodiment the compositions of the present inventions comprise an ionic or ionizable excipient. In a further embodiment, the conductivity of the composition comprising the ionic or ionizable excipient is at least about 2.5 mS/cm, at least about 3 mS/cm, at least about 4 mS/cm, at least about 5 mS/cm, about 3 mS/cm, about 4 mS/cm or about 5 mS/cm. In a preferred embodiment, a buffer-free composition of the present invention comprises an ionic or ionizable excipient. In yet another preferred embodiment, a buffer-free composition of the present invention comprising the ionic or ionizable excipient has a conductivity of at least about 2.5 mS/cm, at least about 3 mS/cm, at least about 4 mS/cm, at least about 5 mS/cm, about 3 mS/cm, about 4 mS/cm or about 5 mS/cm.

In certain embodiments, the present invention is directed to stable protein compositions comprising:
a protein; and
at least one excipient selected from the group consisting of hindered amines, anionic aromatics, functionalized amino acids, oligopeptides, low molecular weight aliphatic polyacids, zwitterions, phospholipids, cyclodextrins, polyethylene glycols ("PEG"), gelatins, octanoate, urea, ethanol, glycerin, dextran, xanthan gum, 2-(2-ethoxyethoxy)ethanol, hydroxypropyl cellulose, propylene glycol, a short chain organic acid comprising a carbon chain of 2 to 13 carbons, deoxycholate, sodium nitrate, sodium sulfate, proline, lysine and mixtures thereof, preferably hydroxypropyl-beta-cyclodextrin ("HPβCD"), hydroxypropyl cellulose and polyethylene glycols or mixtures thereof, more preferably HPβCD, wherein the composition is free of a surfactant.

In a preferred embodiment, the amount of protein is from about 1 mg/mL to about 500 mg/mL, more preferably from about 10 mg/mL to about 200 mg/mL and most preferably from about 50 mg/mL to about 120 mg/mL.

In a preferred embodiment, the present invention is directed to stable protein compositions comprising: a protein; and HPβCD; wherein the composition is free of surfactant. In another preferred embodiment, the composition is free of surfactant and polyol. In another preferred embodiment, the composition is free of surfactant and buffer. In another preferred embodiment, the composition is free of surfactant and sugar. In another preferred embodiment, the composition is free of surfactant, polyol, sugar, and buffer.

In a preferred embodiment, the present invention is directed to stable protein compositions comprising: a protein; and HPC; wherein the composition is free of surfactant. In another preferred embodiment, the composition is free of surfactant and polyol. In another preferred embodiment, the composition is free of surfactant and buffer. In another preferred embodiment, the composition is free of surfactant, polyol, and buffer.

In a preferred embodiment, the present invention is directed to stable protein compositions comprising: a protein; and at least one polyethylene glycol; wherein each polyethylene glycol has a molecular weight from 200 daltons to 20 kilodaltons and the composition is free of surfactant. In another preferred embodiment, the composition is free of surfactant and polyol. In another preferred embodiment, the composition is free of surfactant and buffer. In another preferred embodiment, the composition is free of surfactant, polyol, and buffer. In another preferred embodiment, the composition further comprises a short chain organic acid comprising a carbon chain from 2 to 13 carbons.

In a preferred embodiment, hindered amines are selected from the group consisting of imidazole, 1-methylimidazole, 4-methylimidazole, 1-hexyl-3-methylimidazolium chloride, histamine, 4-methylhistamine, alpha-methylhistamine, beta-histine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, anserine, dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane,tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, dicyandiamide-aminomethanephosphonic acid adducts, aminophylline, 3-isobutyl-1-methylxanthine, paraxanthine pentoxifylline and combinations thereof.

In another preferred embodiment, anionic aromatics are selected from the group consisting of salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and salts thereof and combinations thereof.

In another preferred embodiment, functional amino acids are selected from the group consisting of arginine ethyl ester, arginine methyl ester, arginine hydroxyethyl ester, and arginine hydroxypropyl ester and combinations thereof.

In another preferred embodiment, oligopeptides comprise from 2 to 10 peptide units.

In preferred embodiments, the protein is an antibody.

In more preferred embodiments, the antibody is adalimumab.

In a certain embodiment, the present invention is directed to a method of treating a disease selected from the group consisting of rheumatoid arthritis, chronic plaque psoriasis, Crohn's disease, ankylosing spondylitis, psoriatic arthritis, and polyarticular juvenile idiopathic arthritis, preferably rheumatoid arthritis, comprising administering a pharmaceutically effective amount of a composition of the present invention to a subject in need thereof.

The following preferred embodiments are provided solely for illustrative purposes and are not meant to limit the invention in any way.

Materials and Methods

In the Examples below, the chemical and physical stability of the adalimumab protein and the formulation comprising a high concentration of adalimumab is measured using, e.g., SEC, RP, UV, pH, CE-IEF and CE-SDS. However, other analytical methods may also be employed, for example, biophysical techniques such as those described by Jiskoot and Crommelin (Methods for Structural Analysis of Protein Pharmaceuticals, Springer, New York, 2005). Specific examples of such techniques are described below and further include spectroscopic analyses (e.g., second derivative ultraviolet spectroscopy, circular dichroism, Fourier Transform infrared spectroscopy, Raman spectroscopy, fluorescence and phosphorescence spectroscopy), thermal analyses (e.g., differential scanning calorimetry), and size based analyses (e.g., analytical ultracentrifuge, light scattering).

One of skill in the art can readily determine which of these or other suitable techniques may be used in specific situations when assessing the physical characteristics (e.g., stability, aggregation, oxidation, etc.) of the adalimumab protein in particular formulations.

Processing of Humira

Experiments using adalimumab present in commercially available Humira® may be processed according to the following procedures or to those known by one of skill in the art. Humira® material was dialyzed as follows: 100 µL of Humira® was placed into Mini Dialysis units with a 3.5 MWCO and dialyzed in 1 L of formulation buffer for 24 hours at 4 to 8° C. A few samples did experience a small increase in volume due to the dialysis, but never to extent that the concentration of the polysorbate 80 dropped below the CMC (critical micelle concentration).

The protein concentration for each formulation was measured by UV absorbance spectroscopy, using a calculated experimental molar absorptivity based on reported concentration of Humira®, 50 mg/mL. For a number of the formulations the protein concentration was adjusted by using a spin concentrator. The sample was placed in the spin concentrator and rotated at 14,000 RPM for 30 to 60 sees. The protein concentration was then checked with UV. After the targeted protein concentration around 50 mg/mL was reached the samples were filtered through a 0.22 µM sterile filter into sterile vials in a biosafety hood. The samples were then placed on stability at 40° C. for one and two weeks.

Processing of a Proprietary Adalimumab Protein

The formulation studies described herein used a proprietary adalimumab biosimilar protein which did not contain polysorbate 80. The material was dialyzed using 7,000 MWCO Slide-A-Lyzer® in different formulation buffers for 24 hours at a temperature range between 4 to 8° C. After dialysis the protein concentration was measured by UV and sample pH was measured. The target concentration of samples was 50±2.5 mg/mL, which was adjusted if the sample concentration fell out of the above range. Some of the samples did experience an increase in sample volume do to dilution, requiring the concentration of the protein to increase. For these samples the protein concentration was increased by using spin concentrators, usually at 14,000 rpm for 30 to 60 secs. The pH of a number of samples were adjusted using 1M NaOH or 1M HCl to reach the target pH of 5.2.

After the targeted protein concentration and pH of the samples were determined to be within experimental parameters, the samples were filtered through a 0.22 µM sterile filter into sterile vials in a biosafety hood. The samples were then placed on stability at 40° C. for one week and 25° C. for two weeks.

Stability Time Points

A high concentration adalimumab composition is evaluated by for stability by exposing it to storage conditions over time. Storage conditions may be real-time or accelerated. Conditions include, but are not limited to, 1 week at 40° C. (t1/40 C), 6-10 days at 30° C., 2 weeks at 40° C. (t2/40 C), 4 weeks at 25° C. (t4/25 C), 9 weeks at 25° C. (t9/25 C), 13 weeks at 25° C. (t13/25 C), 13 weeks at 5° C. (t13/5 C), and 26 weeks at 5° C. (t26/5 C). Analyses of a high concentration adalimumab composition at a given time point are compared to analyses of the composition at time 0 (t0), before the composition was exposed to storage conditions.

Analytical Methods

Stability of high concentration adalimumab compositions can be measured using any of a variety of well-known methods, such as visual observation, turbidity measurement at 600-700 nm, light scattering, particle counting, electrophoresis, chromatographic methods like size-exclusion, ion-exchange, hydrophobic interaction, and/or reversed phase, structural analyses like CD, FTIR, fluorescence, DSC, and/or UV/VIS, and biological activity assays. Instability can be indicated by any of soluble aggregates, precipitates (insoluble aggregates), gelation, changes in pH, loss of activity. Aggregation can be measured by SEC-HPLC methods, dynamic light scattering, analytical ultracentrifuge, and by electrophoresis. Stresses relevant for the stability studies include storage at elevated temperature, agitation, freeze-thawing, light exposure, etc.

Generally, high levels of monomeric, therapeutically active, adalimumab is present in stable compositions. Conversely, compositions with low levels of adalimumab aggregates and/or degraded adalimumab (e.g. fragments) are also stable.

Size Exclusion Chromatography (SEC)

Size Exclusion Chromatography (SEC) is used to analyze the amount of monomer adalimumab in a composition. SEC is also useful in determining the amount of adalimumab aggregates and/or fragments in a composition.

Cation Exchange Chromatography (CEX)

Cation Exchange Chromatography (CEX) is also used to analyze the amount of monomer adalimumab in a composition. CEX is also useful in determining the amount of adalimumab aggregates and/or fragments in a composition. CEX method parameters known by one of skill in the art may be used for the analysis of adalimumab compositions.

Reverse Phase Chromatography (RP)

Reverse Phase Chromatography (RP) is also used to analyze the amount of monomer adalimumab in a composition. RP is also useful in determining the amount of adalimumab aggregates and/or fragments in a composition. RP method parameters known by one of skill in the art may be used for the analysis of adalimumab compositions.

Asymmetric Flow Field Flow Fractionation (AF4)

Asymmetric flow field flow fractionation (AF4) is a type of asymmetric field flow fractionation. AF4 is a method capable of rapid fractionation and high resolution characterization of various particles including bio-molecules (Giddings, J. C.; Yang, F. J.; Myers, M. N., Flow-field-flow fractionation: a versatile new separation method, 193 *Science* 1244-1245 (1976); Giddings, J. C.; Yang, F. J.; Myers, M. N., Theoretical and experimental characterization of flow field-flow fractionation, 48 *Anal. Chem.* 1126-1132 (1976)). AF4 is capable of separating particles ranging from a few nanometers to a few micrometers. Proteins, aggregates thereof, and fragments thereof are readily separated due to the difference in mobility in a flow field. Field flow fractionation separation occurs in a thin flow channel (comparable to a chromatographic separation column). An aqueous or organic solvent carries the sample through this channel. The flow through the channel, the first force exerted on the sample, is laminar due to the low channel height. A second force is generated perpendicular to the channel flow. In AF4, one side of the flow channel is a membrane and the second force is fluid flow across the channel through the membrane. Particle separation occurs in this system as a result of these two forces. First, the velocity gradient due to the laminar flow within the channel causes particles in the center of the channel to move more quickly along the channel and be separated from those closer to the sides of the channel. Second, the second force forces the sample toward the membrane. Size separation occurs because the smaller molecules diffuse back toward the center of the channel more quickly than larger particles and hence are separated from the larger particles due to the quicker solvent flow toward the center of the channel.

An AF4 set-up may have a number of different detectors, which allow for determining the molar mass, root mean squared radius (of gyration), and second virial coefficient of the eluting compounds. AF4 analysis provides information on the diffusion coefficients, hydrodynamic radius and the shape of the molecules.

UV Absorbance Spectroscopy

UV spectroscopy is used to measure the protein concentration in the samples. Analysis parameters known by one of skill in the art may be used for the analysis of adalimumab compositions.

Mixed Mode Chromatography (MMC)

MMC is a chromatography method generally utilizes at least two different forces to bind proteins and separate a desired protein product from undesired materials that may be present in a composition containing the desired protein along with undesired impurities. These forces can include, for example, electrostatic forces and hydrophobic forces. Therefore, MMC is useful for evaluating the stability of adalimumab by determining the amount of adalimumab monomer present in a formulation.

Two examples of mixed mode resins are Capto® MMC and Capto® Adhere (available from GE Healthcare). Capto® MMC utilizes a ligand attached to a solid support matrix that may interact with the analyte by cation exchange (with its carboxylic group), hydrogen bonding, and hydrophobic interactions. Capto® Adhere is similar to Capto® MMC in that it also employs a ligand which is attached to a solid support matrix. The ligand, N-benzyl-N-methyl ethanol amine, also interacts with the analyte by anion exchange, hydrogen bonding, and hydrophobic interactions. MMC parameters known by one of skill in the art may be used for the evaluation of adalimumab compositions.

Micro-Flow Imaging (MFI)

Micro-Flow Imaging (MFI) is an imaging technology that is used to detect and measure subvisible and visible particulate matter in solutions. The technology captures digital images of particles suspended in a fluid as they pass through a sensing zone, which are automatically analysed to provide a digital archive of particle parameters aspect ratio and intensity. Furthermore, the results are described as the size and count of the particles. MFI is useful for detecting protein, rubber, and polystyrene particles, silicone, and oil droplets in a formulation. Analysis parameters known by one of skill in the art may be used for the analysis of adalimumab compositions.

Reverse Phase-High Performance Liquid Chromatography (RP-HPLC)

RP-HPLC is useful for evaluating the stability of adalimumab in formulations. RP-HPLC analyses detect the amount of adalimumab, and fragments and/or aggregates thereof, present in a formulation. RP method parameter known by one of skill in the art may be used for the analysis of adalimumab compositions.

CE-IEF Analysis

Capillary isoelectric focusing (cIEF) methods known by one of skill in the art may be used for the analysis of adalimumab compositions. For example, cIEF may be conducted as described in the PA 800 plus Application Guide published by Beckman Coulter. A more detailed description can be found in a research article published by Mack et al. The pI markers and adalimumab are detected with absorbance at 280 nm during the mobilization step. The pI of adalimumab is calculated from the resultant regression equation of pI vs. first peak moment obtained from the pI standards.

CE-SDS Analysis

Analysis by CE-SDS methods known by one of skill in the art may be used for the analysis antibody fragment in adalimumab compositions. For example, CE-SDS is conducted under reducing conditions utilizing a method adapted from the SOP published by Beckman-Coulter for determining IgG purity/heterogeneity. Antibody fragments are detected using absorbance at 214 nm (4 Hz acquisition) and time-normalized areas reported for measured peaks.

pH

The pH of a composition is measured according to methods known in the art. For example, the pH of a sample is measured using a mico-pH probe. Before the start of analysis the pH probe is calibrated with three pH standards. The pH values of samples are measured by transferring 60 µL of each sample to 100 uL PCR tube. The micro-pH probe is then submerged into the sample and after the value stabilized it is recorded.

Conductivity

Conductivity of a composition is measured according to methods known in the art. Conductivity meters and cells may be used to determine the conductivity of the aqueous formulation, and should be calibrated to a standard solution before use. Examples of conductivity meters available in the art include MYRON L® Digital (Cole Parmer®), Conductometer (Metrohm AG), and Series 3105/3115 Integrated Conductivity Analyzers (Kemotron).

Hydrodynamic Diameter

The term "hydrodynamic diameter of a protein" as used herein refers to a size determination for proteins in solution using dynamic light scattering (DLS). A DLS-measuring instrument measures the time-dependent fluctuation in the intensity of light scattered from the proteins in solution at a fixed scattering angle. Protein $D_h$ is determined from the intensity autocorrelation function of the time-dependent fluctuation in intensity. Scattering intensity data are processed using DLS instrument software to determine the value for the hydrodynamic diameter and the size distribution of the scattering molecules, i.e. the protein specimen. The hydrodynamic diameter of the protein in solution may be measured using dynamic light scattering (DLS), which is an established analytical method for determining the $D_h$ of proteins.

Viscosity

Viscosity can be measured by methods known to one of skill in the art, including the use of various types of viscometers and rheometers. In a further embodiment the viscometer is a U-tube viscometer, a falling piston viscometer, a rotational viscometer or a bubble viscometer. In an embodiment, the rheometer is a Rheotans, a CaBer, an Acoustic, a Falling Plate, a Capillary/Contraction Flow, a FiSER or a Sentmanat. In a further embodiment, viscosity is measured with a Zahn cup, in which the efflux time is determined or a Ford viscosity cup.

Viscosity of compositions can be measured using any of a variety of well-known methods, such as viscometry, Instron, and measurements of injectability and syringeability.

Solubility

Solubility, such as that of proteins, in compositions can be measured using any of a variety of well-known methods. For example, a protein solution is concentrated to a desired concentration or above using ultrafiltration. The concentration in the clear supernatant is determined for solubility. Protein beyond solubility will either precipitate or form a gel.

Freeze-Thaw Conditions

Compositions for freeze-thaw analyses are prepared on the day of analysis to match with t=0. The samples are frozen at −80° C. between 3 to 7 minutes. The frozen sample are then thawed at room temperature until all the ice has thawed. The freeze and thaw cycle may be repeated (e.g. 5 times) for each sample.

Agitation

To evaluate the stability of adalimumab, formulations are subjected to agitation studies. For example, compositions are agitated at 150 rpm for 24 hours at 4° C. on a rockerplate. A control is prepared and placed next to the rocker plate for each sample that is agitated.

PREFERRED EMBODIMENTS

In certain embodiments, the present invention is directed to stable protein compositions comprising:
adalimumab; and
at least one excipient selected from the group consisting of hindered amines, anionic aromatics, functionalized amino acids, oligopeptides, low molecular weight aliphatic polyacids, zwitterions, phospholipids, cyclodextrins, polyethylene glycols ("PEG"), gelatins, octanoate, urea, ethanol, glycerin, dextran, xanthan gum, 2-(2-ethoxyethoxy)ethanol, hydroxypropyl cellulose, propylene glycol, a short chain organic acid comprising a carbon chain of 2 to 13 carbons, deoxycholate, sodium nitrate, sodium sulfate, proline, lysine and mixtures thereof, preferably hydroxypropyl-beta-cyclodextrin ("HPβCD"), hydroxypropyl cellulose and polyethylene glycols or mixtures thereof, more preferably HPβCD,
wherein the composition is free of a surfactant.

In a preferred embodiment, the present invention is directed to stable protein compositions comprising:
adalimumab; and
HPβCD,
wherein the composition is free of a surfactant and wherein, preferably, the composition is free of a polyol.

In a preferred embodiment, the present invention is directed to stable protein compositions comprising:
adalimumab; and
HPC,
wherein the composition is free of a surfactant and wherein, preferably, the composition is free of a polyol.

In a preferred embodiment, the present invention is directed to stable protein compositions comprising:
adalimumab;
at least one polyethylene glycol; and
a short chain organic acid comprising a carbon chain from 2 to 13 carbons, wherein each polyethylene glycol has a molecular weight from 200 daltons to 20 kilodaltons and wherein the composition is free of a surfactant and wherein, preferably, the composition is free of a polyol.

The invention also provides the following exemplary embodiments:

1. A stable protein composition comprising:
(i) a protein; and
(ii) at least one excipient selected from the group consisting of hindered amines, anionic aromatics, functionalized amino acids, oligopeptides, low molecular weight aliphatic polyacids, zwitterions, phospholipids, cyclodextrins, polyethylene glycols, gelatins, urea, ethanol, glycerin, dextran, xanthan gum, 2-(2-ethoxyethoxy)ethanol, hydroxypropyl cellulose, propylene glycol, deoxycholate, sodium nitrate, sodium sulfate, proline and lysine;
wherein the composition is free of surfactant.

2. The composition of embodiment 1, wherein the composition is free of polyol.

3. The composition of embodiment 1 comprising a short chain organic acid comprising a carbon chain of 2 to 13 carbons.

4. The composition of embodiment 1, wherein the cyclodextrin is selected from the group consisting of an alpha cyclodextrin, a beta cyclodextrin, a gamma cyclodextrin, and a combination thereof.

5. The composition of claim 4, wherein the alpha cyclodextrin, the beta cyclodextrin, and the gamma cyclodextrin is a derivatized cyclodextrin.

6. The composition of claim 5, wherein the derivatized beta cyclodextrin is selected from the group consisting of methyl-beta-cyclodextrins (MβCD), randomly methylated-beta-cyclodextrin (RMβCD), Sulfobutylether-beta-cyclodextrins (SBEβCD), and hydroxypropyl-beta-cyclodextrins (HPβCD).

7. The composition of claim 6, wherein the derivatized beta cyclodextrin is HPβCD.

8. The composition of embodiment 7, wherein HPβCD is present at a concentration selected from the group consisting of about greater than 10 millimolar (mM), about 10 mM to about 150 mM, about 25 mM to about 100 mM, about 50 mM to about 75 mM, about 25 mM, about 50 mM, about 70 mM, about 75 Mm, about 1% w/v and about 3% w/v, wherein w/v denotes weight by total volume of the composition.

9. The composition of embodiment 1, wherein the hydroxypropyl cellulose is present at a concentration selected from the group consisting of about 0.01% to about 20% w/v, about 0.05% to about 10% w/v, about 0.1% to about 5% w/v, about 0.2% to about 2% w/v, about 0.1% to about 5% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, and about 1% w/v, wherein w/v denotes weight by total volume of the composition.

10. The composition of embodiment 1, wherein the hindered amines are selected from the group consisting of imidazole, 1-methylimidazole, 4-methylimidazole, 1-hexyl-3-methylimidazolium chloride, histamine, 4-methylhistamine, alpha-methylhistamine, betahistine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, anserine, dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane,tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, dicyandiamide-aminomethanephosphonic acid adducts, aminophylline, 3-isobutyl-1-methylxanthine, paraxanthine pentoxifylline and combinations thereof.

11. The composition of embodiment 1, wherein the anionic aromatics are selected from the group consisting of salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and salts thereof and combinations thereof.

12. The composition of embodiment 1, wherein the functional amino acids are selected from the group consisting of arginine ethyl ester, arginine methyl ester, arginine hydroxyethyl ester, and arginine hydroxypropyl ester and combinations thereof.

13. The composition of embodiment 1, wherein the oligopeptides comprise from 2 to 10 peptide units.

14. The composition of embodiment 1, wherein the low molecular weight aliphatic polyacids are selected from the group consisting of maleic acid, tartaric acid, glutaric acid, malonic acid, citric acid, ethylenediaminetetraacetic acid (EDTA), aspartic acid, glutamic acid, alendronic acid, etidronic acid, glycolic acid, lactic acid, gluconic acid, and polyacrylic acid, and polyphosphates thereof, polypeptides thereof and salts thereof.

15. The composition of embodiment 1, wherein the at least one excipient comprises at least two polyethylene glycols.

16. The composition of embodiment 15, wherein each of the at least two polyethylene glycols have a molecular weight from 200 Daltons to 20 kilo Daltons.

17. The composition of embodiment 1, wherein the protein is an antibody.

18. The composition of embodiment 17, wherein the antibody is adalimumab or a biosimilar thereof.

19. The composition of embodiment 1, wherein the protein is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

20. The composition of embodiment 1, wherein the composition has a pH of about 4 to about 8.

21. The composition of embodiment 1, wherein the composition exhibits long term stability.

22. The composition of embodiment 1, wherein the composition is a pharmaceutical composition.

23. The composition of embodiment 22, wherein the composition is a liquid composition.

24. The composition of embodiment 23, wherein the liquid composition is suitable for injection into a subject.

25. The composition of embodiment 1, wherein the composition is isotonic or has an osmolality of about 180 to about 420 milliosmolar.

26. The composition of embodiment 1, further comprising a buffer.

27. The composition of embodiment 26, wherein the buffer comprises phosphate, pyrophosphate, citrate, acetate, glutamate, gluconate, histidine, succinate, adipate, maleate, tartrate, and combinations thereof.

28. The composition of embodiment 26, wherein the buffer is histidine.

29. The composition of embodiment 28, wherein the histidine buffer is present at a concentration selected from the group consisting of about 5 millimolar (mM) to about 50 mM, about 10 mM to about 30 mM, about 10 mM, about 20 mM, and about 30 mM.

30. The composition of embodiment 1, comprising a buffer, wherein the composition is (a) free or essentially free of citrate buffer; or (b) free or essentially free of phosphate buffer; or (c) free or essentially free of a buffer composition comprising citrate buffer and phosphate buffer.

31. The composition of embodiment 1, wherein the composition is free of buffer.

32. The composition of embodiment 1, further comprising a stabilizer.

33. The composition of embodiment 32, wherein the stabilizer comprises polyols, amino acids, salts, and combinations thereof.

34. The composition of embodiment 1, further comprising a tonicity agent.

35. The composition of embodiment 35, wherein the tonicity agent comprises salts, amino acids, sugars, polyols, and combinations thereof.

36. The composition of embodiment 1, comprising a salt.

37. The composition of embodiment 35, wherein the salt comprises NaCl, KCl, $Na_2SO_4$, $MgCl_2$, $CaCl_2$), and adipate.

38. The composition of embodiment 37, wherein the salt is present at a concentration selected from the group consisting of 5 to 140 millimolar (mM); not exceeding about 150 mM; not exceeding about 100 mM; not exceeding about 50 mM, not exceeding about 44 mM, not exceeding about 28 mM, not exceeding about 26.35 mM, not exceeding about 10 mM, not exceeding about 5 mM, 5 mM, 10 mM, 20 mM, 25 mM, and 50 mM.

39. The composition of embodiment 1, further comprising an amino acid.

40. The composition of embodiment 39, wherein the amino acid is selected from the group consisting of histidine, glycine, methionine, serine, proline, and arginine.

41. The composition of embodiment 39, wherein the amino acid is histidine.

42. The composition of embodiment 39, wherein the amino acid is glycine.

43. The composition of embodiment 39, wherein the amino acid is arginine.

44. The composition of embodiment 39, wherein the amino acid is a combination of glycine and arginine.

45. The composition of embodiment 39, wherein the amino acid is a combination of histidine and glycine.

46. A stable protein composition comprising:
   (i) adalimumab;
   (ii) buffer; and
   (iii) an excipient selected from the group consisting of hydroxypropyl beta cyclodextrin (HPβCD), dextran (40 kilo Dalton), gelatin, octanoate, hydroxypropyl cellulose (HPC), sodium nitrate, sodium sulfate, propylene glycol, glycerin, ethanol, proline, lysine, and polyethylene glycol 300 (PEG300),
wherein the composition is free of surfactant.

47. The composition of embodiment 46, wherein the composition is free of polyol.

48. The composition of embodiment 46, wherein the protein is an antibody.

49. The composition of embodiment 48, wherein the antibody is adalimumab or a biosimilar thereof.

50. The composition of embodiment 46, wherein the protein is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

51. The composition of embodiment 46, wherein the composition has a pH of about 4 to about 8, or about 5 to about 6.

52. The composition of embodiment 46, wherein the composition exhibits long term stability.

53. The composition of embodiment 46, wherein the composition is a pharmaceutical composition.

54. The composition of embodiment 53, wherein the composition is a liquid composition.

55. The composition of embodiment 54, wherein the liquid composition is suitable for injection into a subject.

56. The composition of embodiment 46, wherein the composition is isotonic or has an osmolality of about 180 to about 420 milliosmolar.

57. The composition of embodiment 46, further comprising a buffer.

58. The composition of embodiment 57, wherein the buffer comprises phosphate, pyrophosphate, citrate, acetate, glutamate, gluconate, histidine, succinate, adipate, maleate, tartrate, or combinations thereof.

59. The composition of embodiment 57, wherein the buffer is histidine.

60. The composition of embodiment 59, wherein the histidine buffer is present at a concentration selected from the group consisting of about 5 millimolar (mM) to about 50 mM, about 10 mM to about 30 mM, about 10 mM, about 20 mM, and about 30 mM.

61. The composition of embodiment 46, further comprising a buffer, wherein the composition is (a) free or essentially free of citrate buffer; or (b) free or essentially free of phosphate buffer; or (c) free or essentially free of a buffer composition comprising citrate buffer and phosphate buffer.

62. The composition of embodiment 46, wherein the composition is free of buffer.

63. The composition of embodiment 46, further comprising a stabilizer.

64. The composition of embodiment 63, wherein the stabilizer comprises polyols, amino acids, salts, and combinations thereof.

65. The composition of embodiment 46, further comprising a tonicity agent.

66. The composition of embodiment 66, wherein the tonicity agent comprises salts, amino acids, sugars, polyols, and combinations thereof.

67. The composition of embodiment 46, further comprising a salt.

68. The composition of embodiment 66, wherein the salt comprises NaCl, KCl, $Na_2SO_4$, $MgCl_2$, $CaCl_2$), and adipate.

69. The composition of embodiment 68, wherein the salt is present at a concentration selected from 5 to 140 millimolar (mM); not exceeding about 150 mM; not exceeding about 100 mM; not exceeding about 50 mM, not exceeding about 44 mM, not exceeding about 28 mM, not exceeding about 26.35 mM, not exceeding about 10 mM, not exceeding about 5 mM, 5 mM, 10 mM, 20 mM, 25 mM, and 50 mM.

70. The composition of embodiment 46, further comprising an amino acid.

71. The composition of embodiment 70, wherein the amino acid is selected from the group consisting of histidine, glycine, methionine, serine, proline, and arginine.

72. The composition of embodiment 70, wherein the amino acid is histidine.

73. The composition of embodiment 70, wherein the amino acid is glycine.

74. The composition of embodiment 70, wherein the amino acid is arginine.

75. The composition of embodiment 70, wherein the amino acid is a combination of glycine and arginine.

76. The composition of embodiment 70, wherein the amino acid is a combination of histidine and glycine.

77. The composition of embodiment 48, wherein HPβCD is present at a concentration selected from the group consisting of about greater than 10 millimolar (mM), about 10 mM to about 150 mM, about 25 mM to about 100 mM, about 50 mM to about 75 mM, about 25 mM, about 50 mM, about 70 mM, about 75 mM, about 1% w/v and about 3% w/v, wherein w/v denotes weight by volume of the total composition.

78. The composition of embodiment 48, wherein the dextran (40 kilo Dalton) is present at a concentration of about 0.5% w/v, wherein w/v denotes weight by volume of the total composition.

79. The composition of embodiment 48, wherein the gelatin is present at a concentration of 0.13% w/v, wherein w/v denotes weight by volume of the total composition.

80. The composition of embodiment 48, wherein the octanoate is present at a concentration of about 10 millimolar.

81. The composition of embodiment 48, wherein the HPC is present at a concentration of about 0.5% w/v, wherein w/v denotes weight by volume of the total composition.

82. The composition of embodiment 48, wherein the sodium nitrate is present at a concentration of about 50 millimolar.

83. The composition of embodiment 48, wherein the sodium sulfate is present at a concentration of about 50 millimolar.

84. The composition of embodiment 48, wherein the propylene glycol is present at a concentration of about 5% v/v, wherein v/v denotes volume by total volume of the composition.

85. The composition of embodiment 48, wherein the glycerin is present at a concentration of about 5% v/v, wherein v/v denotes volume by total volume of the composition.

86. The composition of embodiment 48, wherein the ethanol is present at a concentration of about 5% v/v, wherein v/v denotes volume by total volume of the composition.

87. The composition of embodiment 48, wherein the proline is present at a concentration of about 25 millimolar.

88. The composition of embodiment 48, wherein the lysine is present at a concentration of about 25 millimolar.

89. The composition of embodiment 48, wherein the PEG300 is present at a concentration of about 0.5% w/v to about 5% w/v, about 1% w/v to about 2% w/v, about 1% w/v, or about 2% w/v, wherein w/v denotes weight by volume of the total composition.

90. A stable protein composition comprising:
(i) adalimumab;
(ii) buffer; and
(iii) a combination of excipients selected from the combinations consisting of: polyethylene glycol (PEG)300 and hydroxypropyl beta cyclodextrin (HPβCD);

PEG600 and PEG2000; PEG200 and Propionic Acid; PEG600 and Propionic Acid; PEG2000 and Propionic Acid; PEG200, PEG600 and Propionic Acid; PEG600, PEG2000 and Propionic Acid; PEG200, PEG600 and PEG2000, Propionic Acid; PEG200, PEG600, PEG2000, Ethanol and Lauric Acid; PEG200, PEG600, PEG2000 and Butyric Acid; PEG600 and Valeric Acid; PEG2000 and Valeric Acid; PEG200, PEG600 and Valeric Acid; PEG200, PEG2000 and Valeric Acid; PEG2000 and Caproic Acid; PEG300 and Caproic Acid; PEG600 and Caproic Acid; PEG600 and Caproic Acid; PEG2000 and Caproic Acid; PEG200, PEG600 and Caproic Acid; PEG200, PEG600, PEG2000 and Caproic Acid; PEG300, HPβCD and Caproic Acid; PEG300 and HPβCD, Caproic Acid and Arginine; and PEG 2000, Caproic Acid and Arginine, wherein the composition is free of surfactant.

91. The composition of embodiment 90, wherein the composition is free of polyol.

92. The composition of embodiment 90, wherein the protein is an antibody.

93. The composition of embodiment 92, wherein the antibody is adalimumab or a biosimilar thereof.

94. The composition of embodiment 90, wherein the protein is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

95. The composition of embodiment 90, wherein the composition has a pH of about 4 to about 8, or about 5 to about 6.

96. The composition of embodiment 90, wherein the composition exhibits long term stability.

97. The composition of embodiment 90, wherein the composition is a pharmaceutical composition.

98. The composition of embodiment 97, wherein the composition is a liquid composition.

99. The composition of embodiment 98, wherein the liquid composition is suitable for injection into a subject.

100. The composition of embodiment 90, wherein the composition is isotonic or has an osmolality of about 180 to about 420 milliosmolar.

101. The composition of embodiment 90, comprising a buffer.

102. The composition of embodiment 101, wherein the buffer comprises phosphate, pyrophosphate, citrate, acetate, glutamate, gluconate, histidine, succinate, adipate, maleate, tartrate, or combinations thereof.

103. The composition of embodiment 101, wherein the buffer is histidine.

104. The composition of embodiment 103, wherein the histidine buffer is present at a concentration selected from the group consisting of about 5 millimolar (mM) to about 50 mM, about 10 mM to about 30 mM, about 10 mM to about 20 mM, and about 30 mM.

105. The composition of embodiment 90, comprising a buffer, wherein the composition is (a) free or essentially free of citrate buffer; or (b) free or essentially free of phosphate buffer; or (c) free or essentially free of a buffer composition comprising citrate buffer and phosphate buffer.

106. The composition of embodiment 90, wherein the composition is free of buffer.

107. The composition of embodiment 90, further comprising a stabilizer.

108. The composition of embodiment 107, wherein the stabilizer comprises polyols, amino acids, salts, and combinations thereof.

109. The composition of embodiment 90, further comprising a tonicity agent.

110. The composition of embodiment 110, wherein the tonicity agent comprises salts, amino acids, sugars, polyols, and combinations thereof.

111. The composition of embodiment 90, further comprising a salt.

112. The composition of embodiment 110, wherein the salt comprises NaCl, KCl, $Na_2SO_4$, $MgCl_2$, $CaCl_2$, and adipate.

113. The composition of embodiment 112, wherein the salt is present at a concentration selected from 5 to 140 millimolar (mM); not exceeding about 150 mM; not exceeding about 100 mM; not exceeding about 50 mM, not exceeding about 44 mM, not exceeding about 28 mM, not exceeding about 26.35 mM, not exceeding about 10 mM, not exceeding about 5 mM, 5 mM, 10 mM, 20 mM, 25 mM, and 50 mM.

114. The composition of embodiment 90, further comprising an amino acid.

115. The composition of embodiment 114, wherein the amino acid is selected from the group consisting of histidine, glycine, methionine, serine, proline, and arginine.

116. The composition of embodiment 114, wherein the amino acid is histidine.

117. The composition of embodiment 114, wherein the amino acid is glycine.

118. The composition of embodiment 114, wherein the amino acid is arginine.

119. The composition of embodiment 114, wherein the amino acid is a combination of glycine and arginine.

120. The composition of embodiment 114, wherein the amino acid is a combination of histidine and glycine.

121. A stable protein composition consisting of:
(i) adalimumab;
(ii) polyethylene glycol 300 (PEG300);
(iii) hydroxypropyl beta cyclodextrin (HPβCD);
(iv) Caproic Acid; and
(v) Arginine,
wherein the composition is free of surfactant.

122. The composition of embodiment 121, wherein adalimumab is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

123. The composition of embodiment 121, wherein the composition has a pH of about 4 to about 8, or about 5 to about 6.

124. The composition of embodiment 121, wherein the composition has a pH of about 5.2.

125. The composition of embodiment 121, wherein the composition exhibits long term stability.

126. The composition of embodiment 121, wherein the composition is a pharmaceutical composition.

127. The composition of embodiment 126, wherein the composition is a liquid composition.

128. The composition of embodiment 127, wherein the liquid composition is suitable for injection into a subject.

129. The composition of embodiment 121, wherein the composition is isotonic or has an osmolality of about 180 to about 420 milliosmolar.

130. A stable protein composition comprising:
(i) adalimumab;
(ii) buffer;
(iii) stabilizer;
(iv) hydroxypropyl beta cyclodextrin (HPβCD); and
(v) optionally salt,
wherein the composition is free of surfactant.

131. The composition of embodiment 130, wherein adalimumab is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

132. The composition of embodiment 130, wherein the composition has a pH of about 4 to about 8, or about 5 to about 6.

133. The composition of embodiment 130, wherein the composition has a pH of about 5.2.

134. The composition of embodiment 130, wherein the composition is free of polyol.

135. The composition of embodiment 130, wherein the composition exhibits long term stability.

136. The composition of embodiment 130, wherein the composition is a pharmaceutical composition.

137. The composition of embodiment 136, wherein the composition is a liquid composition.

138. The composition of embodiment 137, wherein the liquid composition is suitable for injection into a subject.

139. The composition of embodiment 130, wherein the composition is isotonic or has an osmolality of about 180 to about 420 mOsM.

140. The composition of embodiment 130, wherein the buffer is histidine.

141. The composition of embodiment 140, wherein histidine is present at a concentration of about 20 millimolar (mM) to 30 mM.

142. The composition of embodiment 130, wherein the stabilizer is an amino acid selected from the group consisting of glycine, methionine, serine, proline, arginine, and combinations thereof.

143. The composition of embodiment 142, wherein the amino acid is glycine.

144. The composition of embodiment 143, wherein glycine is present at a concentration of about 100 millimolar (mM) to about 200 mM.

145. The composition of embodiment 130, wherein HPβCD is present at a concentration of about 25 millimolar (mM) to about 70 mM.

146. The composition of embodiment 130, wherein the salt comprises NaCl, KCl, $Na_2SO_4$, $MgCl_2$, $CaCl_2$), and adipate.

147. The composition of embodiment 146, wherein the salt is NaCl.

148. The composition of embodiment 147, wherein the NaCl is present at a concentration selected from about 20 millimolar (mM) to about 30 mM.

149. A stable protein composition comprising 50 milligrams per milliliter (mg/mL) adalimumab, 20 millimolar (mM) histidine, 180 mM glycine, and 25 mM hydroxypropyl beta cyclodextrin (HPβCD), wherein the composition is free of surfactant.

150. The composition of embodiment 149 comprising 25 mM NaCl.

151. The composition of embodiment 149, wherein the composition is free of polyol.

152. The composition of embodiment 149, wherein the composition has a pH of about 5.2.

153. A stable protein composition comprising 50 milligrams per milliliter (mg/mL) adalimumab, 20 millimolar (mM) histidine, 140 mM glycine, and 50 mM hydroxypropyl beta cyclodextrin (HPβCD), wherein the composition is free of surfactant.

154. The composition of embodiment 153 comprising 25 mM NaCl.

155. The composition of embodiment 153, wherein the composition is free of polyol.

156. The composition of embodiment 153, wherein the composition has a pH of about 5.2.

157. A stable protein composition comprising milligrams per milliliter (mg/mL) adalimumab, 20 millimolar (mM) histidine, 100 mM glycine, and 70 mM hydroxypropyl beta cyclodextrin (HPβCD), wherein the composition is free of surfactant.

158. The composition of embodiment 157 comprising 25 mM NaCl.

159. The composition of embodiment 157, wherein the composition is free of polyol.

160. The composition of embodiment 157, wherein the composition has a pH of about 5.2.

161. A stable protein composition comprising:
(i) adalimumab;
(ii) stabilizer;
(iii) hydroxypropyl beta cyclodextrin (HPβCD); and
(iv) optionally salt,
wherein the composition is free of surfactant and buffer.

162. The composition of embodiment 161, wherein adalimumab is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

163. The composition of embodiment 161, wherein the composition has a pH of about 4 to about 8, or about 5 to about 6.

164. The composition of embodiment 161, wherein the composition has a pH of about 5.2.

165. The composition of embodiment 161, wherein the composition is free of polyol.

166. The composition of embodiment 161, wherein the composition exhibits long term stability.

167. The composition of embodiment 161, wherein the composition is a pharmaceutical composition.

168. The composition of embodiment 167, wherein the composition is a liquid composition.

169. The composition of embodiment 168, wherein the liquid composition is suitable for injection into a subject.

170. The composition of embodiment 161, wherein the composition is isotonic or has an osmolality of about 180 to about 420 milliosmolar.

171. The composition of embodiment 161, wherein the stabilizer is an amino acid selected from the group consisting of histidine, glycine, methionine, serine, proline, arginine, and combinations thereof.

172. The composition of embodiment 171, wherein the amino acid is glycine.

173. The composition of embodiment 172, wherein glycine is present at a concentration of about 100 millimolar (mM) to about 300 mM.

174. The composition of embodiment 171, wherein the amino acid is glycine and arginine.

175. The composition of embodiment 174, wherein glycine is present at a concentration of about 100 millimolar (mM) to about 300 mM and arginine is present at a concentration of about 10 mM to about 100 mM.

176. The composition of embodiment 161, wherein HPβCD is present at a concentration of about 25 millimolar (mM) to about 70 mM.

177. The composition of embodiment 161, wherein the salt comprises NaCl, KCl, $Na_2SO_4$, $MgCl_2$, $CaCl_2$), and adipate.

178. The composition of embodiment 177, wherein the salt is NaCl.

179. The composition of embodiment 178, wherein the NaCl is present at a concentration selected from about 10 millimolar (mM) to about 100 mM.

180. A stable protein composition comprising 50 milligrams per milliliter (mg/mL) adalimumab, 160 millimolar (mM) glycine, 25 mM NaCl, and 50 mM hydroxypropyl beta cyclodextrin (HPβCD), wherein the composition is free of surfactant and buffer.

181. The composition of embodiment 180, wherein the composition is free of polyol.

182. The composition of embodiment 180, wherein the composition has a pH of about 5.2.

183. A stable protein composition comprising 50 milligrams per milliliter (mg/mL) adalimumab, 240 millimolar (mM) glycine, 45 mM arginine, and 50 mM hydroxypropyl beta cyclodextrin (HPβCD), wherein the composition is free of surfactant and buffer.

184. The composition of embodiment 183 comprising 25 mM NaCl.

185. The composition of embodiment 183, wherein the composition is free of polyol.

186. The composition of embodiment 183, wherein the composition has a pH of about 5.2.

187. A stable protein composition comprising 50 milligrams per milliliter (mg/mL) adalimumab, 240 millimolar (mM) glycine, 30 mM NaCl, and 50 mM hydroxypropyl beta cyclodextrin (HPβCD), wherein the composition is free of surfactant and buffer.

188. The composition of embodiment 187, wherein the composition is free of polyol.

189. The composition of embodiment 187, wherein the composition has a pH of about 5.2.

190. A stable protein composition comprising:
(i) a protein; and
(ii) an excipient that does not form micelles which is not an amino acid, polyol, or salt,
wherein the composition is free of surfactant; and the surface tension of the composition is not less than 75% of the surface tension of the same composition without the excipient that does not form micelles.

191. The composition of embodiment 190, wherein the surface tension of the composition is not less than 85% of the surface tension of the same composition without the excipient that does not form micelles.

192. The composition of embodiment 190, wherein the surface tension of the composition is not less than 90% of the surface tension of the same composition without the excipient that does not form micelles.

193. The composition of embodiment 190, wherein the surface tension of the composition is not less than 95% of the surface tension of the same composition without the excipient that does not form micelles.

194. The composition of embodiment 190 comprising a short chain organic acid comprising a carbon chain of 2 to 13 carbons.

195. The composition of embodiment 190, wherein the composition is free of polyol.

196. The composition of embodiment 190, wherein the excipient which does not form micelles is selected from the group comprising hindered amines, anionic aromatics, functionalized amino acids, oligopeptides, low molecular weight aliphatic polyacids, zwitterions, phospholipids, cyclodextrins, polyethylene glycols, gelatins, urea, ethanol, glycerin, dextran, xanthan gum, 2-(2-ethoxyethoxy)ethanol, hydroxypropyl cellulose, propylene glycol, deoxycholate, sodium nitrate, sodium sulfate, proline and lysine.

197. The composition of embodiment 196, wherein the hindered amines are selected from the group consisting of imidazole, 1-methylimidazole, 4-methylimidazole, 1-hexyl-3-methylimidazolium chloride, histamine, 4-methylhistamine, alpha-methylhistamine, betahistine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, anserine, dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane,tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, dicyandiamide-aminomethanephosphonic acid adducts, aminophylline, 3-isobutyl-1-methylxanthine, paraxanthine pentoxifylline and combinations thereof.

198. The composition of embodiment 196, wherein the anionic aromatics are selected from the group consisting of salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and salts thereof and combinations thereof.

199. The composition of embodiment 196, wherein the functional amino acids are selected from the group consisting of arginine ethyl ester, arginine methyl ester, arginine hydroxyethyl ester, and arginine hydroxypropyl ester and combinations thereof.

200. The composition of embodiment 196, wherein the oligopeptides comprise from 2 to 10 peptide units.

201. The composition of embodiment 196, wherein the low molecular weight aliphatic polyacids are selected from the group consisting of maleic acid, tartaric acid, glutaric acid, malonic acid, citric acid, ethylenediaminetetraacetic acid (EDTA), aspartic acid, glutamic acid, alendronic acid, etidronic acid, glycolic acid, lactic acid, gluconic acid, and polyacrylic acid, and polyphosphates thereof, polypeptides thereof and salts thereof.

202. The composition of embodiment 190, wherein the excipient which does not form micelles comprises at least two polyethylene glycols 203. The composition of embodiment 202, wherein each of polyethylene glycols have a molecular weight from 200 daltons to 20 kilodaltons.

204. The composition of embodiment 190, wherein the protein is an antibody.

205. The composition of embodiment 204, wherein the antibody is adalimumab or a biosimilar thereof.

206. The composition of embodiment 190, wherein the composition has a pH of about 4 to about 8.

207. The composition of embodiment 190, wherein the composition exhibits long term stability.

208. The composition of embodiment 190, wherein the composition is a pharmaceutical composition.

209. The composition of embodiment 208, wherein the composition is a liquid composition.

210. The composition of embodiment 209, wherein the liquid composition is suitable for injection into a subject.

211. A stable protein composition comprising:
 (i) a protein;
 (ii) at least one polyethylene glycol; and
 (iii) a short chain organic acid comprising a carbon chain of 2 to 13 carbons;
wherein the polyethylene glycol has a molecular weight from 200 daltons to 20 kilodaltons; and wherein the composition is free of a surfactant.

212. The composition of embodiment 211, wherein the composition is free of polyol.

213. The composition of embodiment 211 further comprising at least one excipient selected from the group consisting of hindered amines, anionic aromatics, functionalized amino acids, oligopeptides, short-chain organic acids, low molecular weight aliphatic polyacids, zwitterions, phospholipids, cyclodextrins, gelatins, urea, ethanol, glycerin, dextran, xanthan gum, 2-(2-ethoxyethoxy)ethanol, hydroxypropyl cellulose, propylene glycol, deoxycholate, sodium nitrate, sodium sulfate, proline and lysine.

214. The composition of embodiment 213, wherein the cyclodextrin is selected from the group consisting of an alpha cyclodextrin, a beta cyclodextrin, a gamma cyclodextrin, and a combination thereof.

215. The composition of claim 214, wherein the alpha cyclodextrin, beta cyclodextrin, or gamma cyclodextrin is a derivatized cyclodextrin.

216. The composition of claim 215, wherein the derivatized beta cyclodextrin is selected from the group consisting of methyl-beta-cyclodextrins (MβCD), randomly methylated-beta-cyclodextrin (RMβCD), Sulfobutylether-beta-cyclodextrins (SBEβCD), and hydroxypropyl-beta-cyclodextrins (HPβCD).

217. The composition of claim 216, wherein the derivatized beta cyclodextrin is HPβCD.

218. The composition of embodiment 217, wherein HPβCD is present at a concentration selected from the group consisting of about greater than 10 millimolar (mM), about 10 mM to about 150 mM, about 25 mM to about 100 mM, about 50 mM to about 75 mM, about 25 mM to about 50 mM, about 70 mM, about 75 mM, about 1% w/v and about 3% w/v, wherein w/v denotes weight by volume of the total composition.

219. The composition of embodiment 213, wherein the hydroxypropyl cellulose is present at a concentration selected from the group consisting of about 0.01% to about 20% w/v, about 0.05% to about 10% w/v, about 0.1% to about 5% w/v, about 0.2% to about 2% w/v, about 0.1% to about 5% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, and about 1% w/v, wherein w/v denotes weight by volume of the total composition.

220. The composition of embodiment 213, wherein the hindered amines are selected from the group consisting of imidazole, 1-methylimidazole, 4-methylimidazole, 1-hexyl-3-methylimidazolium chloride, histamine, 4-methylhistamine, alpha-methylhistamine, betahistine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, anserine, dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane,tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, dicyandiamide-aminomethanephosphonic acid adducts, aminophylline, 3-isobutyl-1-methylxanthine, paraxanthine pentoxifylline and combinations thereof.

221. The composition of embodiment 213, wherein the anionic aromatics are selected from the group consisting of salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and salts thereof and combinations thereof.

222. The composition of embodiment 213, wherein the functional amino acids are selected from the group consisting of arginine ethyl ester, arginine methyl ester, arginine hydroxyethyl ester, and arginine hydroxypropyl ester and combinations thereof.

223. The composition of embodiment 213, wherein the oligopeptides comprise from 2 to 10 peptide units.

224. The composition of embodiment 213, wherein the low molecular weight aliphatic polyacids are selected from the group consisting of maleic acid, tartaric acid, glutaric acid, malonic acid, citric acid, ethylenediaminetetraacetic acid (EDTA), aspartic acid, glutamic acid, alendronic acid, etidronic acid, glycolic acid, lactic acid, gluconic acid, and polyacrylic acid, and polyphosphates thereof, polypeptides thereof and salts thereof.

225. The composition of embodiment 213, wherein the at least one excipient comprises at least two polyethylene glycols.

226. The composition of embodiment 225, wherein each of the at least two polyethylene glycols have a molecular weight from 200 daltons to 20 kilodaltons.

227. The composition of embodiment 211, wherein the protein is an antibody.

228. The composition of embodiment 227, wherein the antibody is adalimumab or a biosimilar thereof.

229. The composition of embodiment 211, wherein the protein is present at a concentration selected from the group consisting of about 1 milligram per milliliter (mg/mL) to about 500 mg/mL, about 10 mg/mL to about 200 mg/mL, about 25 mg/mL to about 120 mg/mL, about 50 mg/mL to about 100 mg/mL, about 20 mg/mL, about 25 mg/mL, about 50 mg/mL, about 75 mg/mL, and about 100 mg/mL.

230. The composition of embodiment 211, wherein the composition has a pH of about 4 to about 8.

231. The composition of embodiment 211, wherein the composition exhibits long term stability.

232. The composition of embodiment 211, wherein the composition is a pharmaceutical composition.

233. The composition of embodiment 232, wherein the composition is a liquid composition.

234. The composition of embodiment 233, wherein the liquid composition is suitable for injection into a subject.

235. The composition of embodiment 211, wherein the composition is isotonic or has an osmolality of about 180 to about 420 milliosmolar.

236. The composition of embodiment 211, further comprising a buffer.

237. The composition of embodiment 236, wherein the buffer comprises phosphate, pyrophosphate, citrate, acetate, glutamate, gluconate, histidine, succinate, adipate, maleate, tartrate, or combinations thereof.

238. The composition of embodiment 236, wherein the buffer is histidine.

239. The composition of embodiment 238, wherein the histidine buffer is present at a concentration selected from the group consisting of about 5 millimolar (mM) to about 50 mM, about 10 mM to about 30 mM, about 10 mM to about 20 mM, and about 30 mM.

240. The composition of embodiment 211, further comprising a buffer, wherein the composition is (a) free or essentially free of citrate buffer; or (b) free or essentially free of phosphate buffer; or (c) free or essentially free of a buffer composition comprising citrate buffer and phosphate buffer.

241. The composition of embodiment 211, wherein the composition is free of buffer.

242. The composition of embodiment 211, further comprising a stabilizer.

243. The composition of embodiment 242, wherein the stabilizer comprises polyols, amino acids, salts, and combinations thereof.

244. The composition of embodiment 211, further comprising a tonicity agent.

245. The composition of embodiment 245, wherein the tonicity agent comprises salts, amino acids, sugars, polyols, and combinations thereof.

246. The composition of embodiment 211, further comprising a salt.

247. The composition of embodiment 245, wherein the salt comprises NaCl, KCl, Na$_2$SO$_4$, MgCl$_2$, CaCl$_2$), and adipate.

248. The composition of embodiment 247, wherein the salt is present at a concentration selected from 5 to 140 millimolar (mM); not exceeding about 150 mM; not exceeding about 100 mM; not exceeding about 50 mM, not exceeding about 44 mM, not exceeding about 28 mM, not exceeding about 26.35 mM, not exceeding about 10 mM, not exceeding about 5 mM, 5 mM, 10 mM, 20 mM, 25 mM, and 50 mM.

249. The composition of embodiment 211, comprising an amino acid.

250. The composition of embodiment 249, wherein the amino acid is selected from the group consisting of histidine, glycine, methionine, serine, proline, and arginine.

251. The composition of embodiment 249, wherein the amino acid is histidine.

252. The composition of embodiment 249, wherein the amino acid is glycine.

253. The composition of embodiment 249, wherein the amino acid is arginine.

254. The composition of embodiment 249, wherein the amino acid is a combination of glycine and arginine.

255. The composition of embodiment 249, wherein the amino acid is a combination of histidine and glycine.

256. A method of treating a disease selected from the group consisting of rheumatoid arthritis, chronic plaque psoriasis, Crohn's disease, ankylosing spondylitis, psoriatic arthritis, and polyarticular juvenile idiopathic arthritis comprising administering a pharmaceutically effective amount of a composition of embodiments 1 to 255 to a subject in need thereof.

257. The method of embodiment 256, wherein the disease is rheumatoid arthritis.

The following Examples are provided solely for illustrative purposes and are not meant to limit the invention in any way.

EXAMPLES

Formulations

The following formulations are used to evaluate and compare the performance of various non-surfactant excipients.

TABLE 1

Base and Control Formulations

| Name | Formulation |
|---|---|
| NSF1 | 50 mg/mL adalimumab, 30 mM histidine, 20 mM arginine, 240 mM glycine, pH 5.2 |
| NSF2 | 50 mg/mL adalimumab, 30 mM histidine, 15 mM NaCl, 240 mM glycine, pH 5.2 |
| NBS1 | 50 mg/mL adalimumab, 160 mM glycine, 25 mM NaCl, pH 5.2 |
| NBS2 | 50 mg/mL adalimumab, 240 mM glycine, 45 mM arginine, pH 5.2 |
| NBS3 | 50 mg/mL adalimumab, 240 mM glycine, 30 mM NaCl, pH 5.2 |
| SF1 | 50 mg/mL adalimumab, 30 mM histidine, 160 mM glycine, 44 mM NaCl, 0.1% polysorbate 80, pH 5.3 |
| Humira® 50 mg/mL | 50 mg/mL adalimumab, 1.3 mg/mL citric acid monohydrate, 1.525 mg/mL dibasic sodium phosphate dihyrdate, 12 mg/mL mannitol, 0.8625 mg/mL monobasic sodium phosphate dihyrdate, 1.0 mg/mL polysorbate 80, 6.1625 mg/mL sodium chloride and 0.3 mg/mL sodium citrate, pH 5.2 |

Formulations #1-17 of Table 2 and Formulations #C1-45 of Table 3 contain the same ingredients as NSF1 listed above in the same concentrations except the listed excipients in Table 1 and 2 are added at the listed concentrations. Formulations #C46-49 of Table 2 contain only the ingredients listed in the table.

TABLE 2

Formulations containing single non-surfactant excipients

| | Excipient |
|---|---|
| #1 | 25 mM HPβCD |
| #2 | 3 mM HPβCD |
| #3 | 0.5% Dextran (40 kD) |
| #4 | 0.13% Gelatin |
| #5 | 10 mM Octanoate |
| #6 | 0.5% Hydroxypropyl cellulose (HPC) |
| #7 | 50 mM Sodium nitrate |
| #8 | 50 mM Sodium sulfate |
| #9 | 5% v/v Propylene glycol |
| #10 | 5% v/v Glycerin |
| #11 | 5% v/v Ethanol |
| #12 | 25 mM Proline |
| #13 | 25 mM Lysine |
| #14 | 1% HPβCD |
| #15 | 2% HPβCD |
| #16 | 1% PEG300 |
| #17 | 2% PEG300 |

TABLE 3

Formulations containing non-surfactant excipient combinations

| | Excipients |
|---|---|
| #C1 | 0.75% PEG300 + 0.75% HPβCD |
| #C2 | 1% PEG300 + 1% HPβCD |
| #C3 | 1% PEG600 + 0.1% PEG2000 |
| #C4 | 2% PEG200 + 1% Propionic Acid |
| #C5 | 10% PEG600 + 1% Propionic Acid |
| #C6 | 15% PEG600 + 5% Propionic Acid |
| #C7 | 0.01% PEG2000 + 1% Propionic Acid |
| #C8 | 10% PEG2000 + 1% Propionic Acid |
| #C9 | 2% PEG200 + 1% PEG600 + 1% Propionic Acid |
| #C10 | 5% PEG200 + 5% PEG600 + 1% Propionic Acid |
| #C11 | 1% PEG600 + 0.01% PEG2000 + 1% Propionic Acid |
| #C12 | 10% PEG200 + 2.5% PEG600 + 1% Propionic Acid |
| #C13 | 2% PEG200 + 1% PEG600 + 0.01% PEG2000 + 1% Propionic Acid |
| #C14 | 2% PEG200 + 1% PEG600 + 0.1% PEG2000 + 2.5% EtOH + 0.025% Lauric Acid |
| #C15 | 2% PEG200 + 1% PEG600 + 0.1% PEG2000 + 0.5% EtOH + 0.005% Lauric Acid |
| #C16 | 2% PEG200 + 1% PEG600 + 0.01% PEG2000 + 1% Butyric Acid |
| #C17 | 10% PEG600 + 1% Valeric Acid |
| #C18 | 15% PEG600 + 5% Valeric Acid |
| #C19 | 10% PEG2000 + 1% Valeric Acid |
| #C20 | 5% PEG200 + 5% PEG600 + 1% Valeric Acid |
| #C21 | 10% PEG200 + 2.5% PEG2000 + 1% Valeric Acid |
| #C22 | 5% PEG2000 + 0.05% Caproic Acid |
| #C23 | 2.5% PEG300 + 0.005% Caproic Acid |
| #C24 | 10% PEG600 + 1% Caproic Acid |
| #C25 | 15% PEG600 + 5% Caproic Acid |
| #C26 | 10% PEG2000 + 0.05% Caproic Acid |
| #C27 | 10% PEG2000 + 1% Caproic Acid |
| #C28 | 5% PEG200 + 5% PEG600 + 1% Caproic Acid |
| #C29 | 2% PEG200 + 1% PEG600 + 0.01% PEG2000 + 0.05% Caproic Acid |
| #C30 | 2% PEG200 + 1% PEG600 + 0.1% PEG2000 + 1% Caproic Acid |
| #C31 | 2% PEG200 + 1% PEG600 + 2% PEG2000 + 1% Caproic Acid |
| #C32 | 2% PEG200 + 1% PEG600 + 2% PEG2000 + 0.5% Caproic Acid |
| #C33 | 2% PEG200 + 1% PEG600 + 2% PEG2000 + 0.25% Caproic Acid |
| #C34 | 10% PEG200 + 2.5% PEG600 + 0.01% PEG2000 + 1% Caproic Acid |
| #C35 | 0.75% PEG300 + 0.75% HPβCD + 0.25% Caproic Acid |
| #C36 | 0.75% PEG300 + 0.75% HPβCD + 0.05% Caproic Acid |
| #C37 | 0.75% PEG300 + 0.75% HPβCD + 0.05% Caproic Acid + 50 mM Arginine |
| #C38 | 1% PEG300 + 1% HPβCD + 0.005% Caproic Acid |

TABLE 3-continued

Formulations containing non-surfactant excipient combinations

| | Excipients |
|---|---|
| #C39 | 1% PEG300 + 1% HPβCD + 0.05% Caproic Acid |
| #C40 | 1% PEG300 + 1% HPβCD + 0.01% Caproic Acid |
| #C41 | 5% PEG300 + 0.5% HPβCD + 0.05% Caproic Acid |
| #C42 | 10% PEG300 + 0.5% HPβCD + 0.05% Caproic Acid |
| #C43 | 10% PEG300 + 0.25% HPβCD + 0.05% Caproic Acid |
| #C44 | 15% PEG300 + 0.25% HPβCD + 0.05% Caproic Acid |
| #C45 | 10% PEG 2000 + 0.05% Caproic Acid + 25 mM Arginine |
| #C46 | 50 mg/mL adalimumab + 0.75% PEG300 + 0.75% HPβCD + 0.05% Caproic Acid + 100 mM Arginine |
| #C47 | 90 mg/mL adalimumab + 0.75% PEG300 + 0.75% HPβCD + 0.05% Caproic Acid + 100 mM Arginine |
| #C48 | 50 mg/mL adalimumab + 0.75% PEG300 + 0.75% HPβCD + 0.05% Caproic Acid + 150 mM Arginine |
| #C49 | 50 mg/mL adalimumab + 0.75% PEG300 + 0.75% HPβCD + 0.05% Caproic Acid + 200 mM Arginine |

Example 1. Stability Testing of Single Excipient Formulations

Method

Formulations #1-13 of Table 2 were each filled into multiple pre-filled syringes. For each formulation, multiple syringes were filled that contained a silicone coating on the interior surface and multiple syringes were filled that did not contain a silicone coating. The syringes were then packed into cardboard containers separated by corrugated cardboard. The containers were shipped at 2-8° C. over 1,000 miles by truck over paved roads. After reaching their destination the syringes were inspected for visible particles. The results of this inspection are in Table 4 below.

Formulations #1, 2 and 6, which contained little to no visible particles, were then subjected to a dropping test. The dropping test took place at around 23° C. and consisted of dropping the cardboard containers holding the pre-filled syringes a total of 16 times from a height of 36 inches. The 16 drops consisted of: 1) dropping the container on each of its 6 faces; 2) dropping the container on each of the 4 edges with the needle points in the horizontal position; 3) dropping the container on 1 edge with the needle points facing upward; 4) dropping the container on 1 edge with the needle points facing downward; 5) dropping the container on 2 separate corners with the needle points facing downward; and 6) dropping the container on 2 separate corners with the needle point facing upward. Results of the dropping test are in Table 5.

Following the dropping test Formulations #1, 2 and 6 were analyzed for sub-visible particle Sub-visible particle content was determined using micro-flow imaging ("MFI").

TABLE 4

Visual appearance of formulations after shipping

| Formulation | Visual Appearance |
|---|---|
| NSF1 | Visible Particles |
| 1 | Slightly Opalescent |
| 2 | Slightly Opalescent, 1-2 Visible Particles |
| 3 | Slightly Opalescent, Visible Particles |
| 4 | Slightly Opalescent, Visible Particles |
| 5 | Visible Particles |
| 6 | Slightly Opalescent |
| 7 | Slightly Opalescent, Visible Particles |
| 8 | Slightly Opalescent, Visible Particles |
| 9 | Visible Particles |

TABLE 4-continued

Visual appearance of formulations after shipping

| Formulation | Visual Appearance |
|---|---|
| 10 | Visible Particles |
| 11 | Visible Particles |
| 12 | Visible Particles |
| 13 | Visible Particles |

TABLE 5

Sub-visible particle content after drop test

Total Particles (counts/mL)

| Formulation | All | ≥2 uM | ≥5 uM | ≥10 uM | ≥25 uM |
|---|---|---|---|---|---|
| #1$^{ND}$ | 25401 | 6381 | 1586 | 331 | 0 |
| #1 | 144774 | 53017 | 5751 | 230 | 12 |
| #2$^{ND}$ | 36211 | 10998 | 2244 | 504 | 41 |
| #2 | 255197 | 99077 | 12599 | 1024 | 42 |
| #6$^{ND}$ | 204745 | 43514 | 3292 | 261 | 18 |
| #6 | 793813 | 218438 | 13933 | 212 | 3 |

Non-Silicone (counts/mL)

| Formulation | All | ≥2 uM | ≥5 uM | ≥10 uM | ≥25 uM |
|---|---|---|---|---|---|
| #1$^{ND}$ | 16077 | 2071 | 136 | 28 | 0 |
| #1 | 80210 | 15529 | 318 | 26 | 3 |
| #2$^{ND}$ | 21941 | 3448 | 530 | 243 | 31 |
| #2 | 133177 | 26147 | 1452 | 281 | 21 |
| #6$^{ND}$ | 124143 | 12695 | 161 | 24 | 0 |
| #6 | 469197 | 68902 | 2012 | 34 | 0 |

Silicone (counts/mL)

| Formulation | All | ≥2 uM | ≥5 uM | ≥10 uM | ≥25 uM |
|---|---|---|---|---|---|
| #1$^{ND}$ | 9324 | 4310 | 1450 | 303 | 0 |
| #1 | 64564 | 37488 | 5433 | 203 | 9 |
| #2$^{ND}$ | 14269 | 7549 | 1714 | 261 | 10 |
| #2 | 122021 | 72930 | 11147 | 742 | 21 |
| #6$^{ND}$ | 80602 | 30819 | 3132 | 237 | 18 |
| #6 | 324616 | 149536 | 11921 | 177 | 3 |

$^{ND}$denotes a "no drop" control test

Results

Formulations #1 and 6 contained no visible particles following shipping. See Table 4. Formulation #2 contained only 1-2 visible particles per syringe. All other formulations contained several visible particles.

After the drop test, Formulations #1 and 2 contained 5 and 3 times fewer sub-visible particles than Formulation #6 in silicone coated syringes, non-coated syringes and overall. See Table 5. Formulation #1, which has a higher concentration of HPβCD than Formulation #2, contained around half as many sub-visible particles as Formulation #2. These results are similar to those for the no drop control tests. HPβCD was found to reduce the number of visible and sub-visible particles in liquid protein formulations better than several other non-surfactant excipients.

Example 2. Reduction Sub-Visible Particles in Surfactant Free Formulations

The impact of surfactant and excipients from Table 2 and Table 3 were evaluated in various formulations. The drop test from Example 1 was repeated on formulations NSF1, NSF2, SF1, #C36, #C27, #1, and #6. These formulations were then subject to a sub-visible particle analysis. The results of this test can be seen in FIG. 1.

Formulations NSF1 and NSF2 had sub-visible particle concentrations of greater than 10,000 counts/mL and about 15,000 counts/mL, respectively. Inclusion of the excipients in formulations #C36 and #C27 resulted in stable formulations evidenced by sub-visible particle concentrations of about 2,500 counts/mL in each formulation after dropping. Additionally, inclusion of the excipients in formulations #1 (25 mM HPβCD) and #6 (0.5% HPC) resulted in stable formulations with sub-visible particle concentrations (counts/mL) less than the surfactant containing SF1 formulation.

These results demonstrate that surfactant free formulations of Table 2 and Table 3 are stable.

Example 3. Mechanical Stress Testing of Various HPβCD Concentrations

Figure 2:
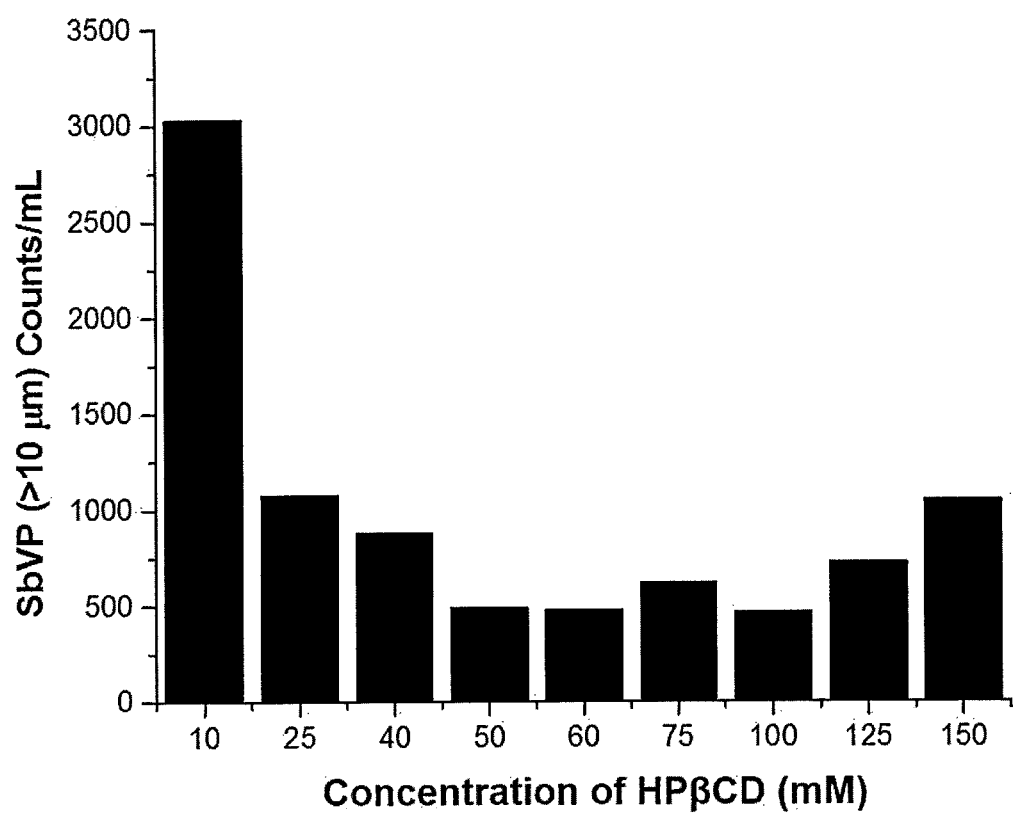
FIG. 2. Sub-visible particle content of formulations containing various amounts of hydroxypropyl-beta-cyclodextrin.

The drop test from Example 1 was repeated on formulations containing various amounts of HPβCD. These formulations were then subject to a sub-visible particle analysis. The results of this test can be seen in FIG. 2.

Concentrations of HPβCD greater than 10 mM resulted in significant reduction in sub-visible particle counts and stable surfactant free formulations. Maximum sub-visible particle reduction for surfactant free adalimumab formulations was found with an HPβCD concentration from 50 to 100 mM.

Example 4. Thermal Stress Testing of Surfactant Free Formulations

Method

Surfactant free formulations are evaluated for stability under thermal stress. Surfactant free formulations optionally comprise a buffer. Surfactant free formulations are compared to the SF1 and Humira formulations described above. Surfactant free formulations with a buffer are listed in table 6, below.

TABLE 6

| Name | Formulation |
|---|---|
| A | 50 mg/mL adalimumab, 20 mM histidine, 180 mM glycine, 25 mM NaCl, 25 mM HPβCD, pH 5.2 |
| B | 50 mg/mL adalimumab, 20 mM histidine, 140 mM glycine, 25 mM NaCl, 50 mM HPβCD, pH 5.2 |
| C | 50 mg/mL adalimumab, 20 mM histidine, 100 mM glycine, 25 mM NaCl, 70 mM HPβCD, pH 5.2 |

Formulations A, B, C, SF1 and Humira® are subjected to four different temperature conditions during an eight-week period. Specifically, 40° C., 25° C., 5° C., and −40° C.

The formulations are periodically tested for soluble aggregates and sub-visible particle content. Fragments and soluble aggregate content is determined using SEC and cation exchange chromatography ("CEX"). Sub-visible particle content is determined using MFI.

Results

Surfactant free formulations, such as formulations A, B, and C, will have sub-visible particle content comparable to, or less than, surfactant containing formulations SF1 and Humira, despite having no surfactant and no polyol. The results of this study will demonstrate that surfactant free formulations with excipient in Tables 2 and 3 are stable formulations.

Example 5. Mechanical Stress Testing of Surfactant Free Formulations

The shipping and drop tests of Example 1 were repeated on formulations #14-17 of Table 2 and Formulations #C1-C49 of Table 3.

TABLE 7

Visual appearance of formulations after shipping

| Formulation | Visible Particles |
|---|---|
| NSF1 | Yes |
| #14 | Yes |
| #15 | Yes |
| #16 | Yes |
| #17 | Yes |
| #C01 | No |
| #C02 | Yes |
| #C03 | Yes |
| #C04 | No |
| #C05 | No |
| #C06 | No |
| #C07 | Yes |
| #C08 | No |
| #C09 | No |
| #C10 | No |
| #C11 | No |
| #C12 | No |
| #C13 | No |
| #C14 | Yes |
| #C15 | No |
| #C16 | Yes |
| #C17 | Opalescent |
| #C18 | Gel formed |
| #C19 | Opalescent |
| #C20 | Opalescent |
| #C21 | Opalescent |
| #C22 | No |
| #C22$^{ND}$ | No |
| #C23 | Opalescent |
| #C24 | Opalescent |

TABLE 7-continued

Visual appearance of formulations after shipping

| Formulation | Visible Particles |
|---|---|
| #C25 | Yes |
| #C26 | No |
| #C26$^{CO}$ | No |
| #C26$^{NA}$ | No |
| #C27 | No |
| #C28 | No |
| #C29 | No |
| #C30 | No |
| #C31 | No |
| #C32 | No |
| #C33 | No |
| #C34 | No |
| #C35 | No |
| #C36 | No |
| #C36$^{R}$ | No |
| #C36$^{ND}$ | No |
| #C36$^{CO}$ | Yes |
| #C36$^{NA}$ | No |
| #C37 | No |
| #C38 | Opalescent |
| #C39 | Yes |
| #C40 | Opalescent |
| #C41 | No |
| #C42 | No |
| #C43 | No |
| #C44 | No |
| #C45 | Yes |
| #C46 | No |
| #C46$^{CO}$ | Yes |
| #C46$^{NA}$ | No |
| #C47 | Yes |
| #C48 | Yes |
| #C49 | Yes |

$^{ND}$denotes a "no drop" control test
$^{CO}$denotes that the air gap in the pre-filled syringe was replaced with $CO_2$
$^{NA}$denotes that the air gap in the pre-filled syringe was removed
$^{R}$denotes a repeat test

TABLE 8

Sub-visible particle content after drop test

| Formula | Total Particles (counts/mL) | | | | | Total Particles (counts/container) | | | | |
|---|---|---|---|---|---|---|---|---|---|---|
| | All | ≥2 uM | ≥5 uM | ≥10 uM | ≥25 uM | All | ≥2 uM | ≥5 uM | ≥10 uM | ≥25 uM |
| #C22$^{ND}$ | 499 | 122 | 25 | 0 | 0 | 399 | 98 | 20 | 0 | 0 |
| #C36$^{ND}$ | 1392 | 307 | 59 | 22 | 12 | 1114 | 246 | 48 | 18 | 10 |
| #C36$^{NA}$ | 11857 | 4517 | 1076 | 205 | 26 | — | — | — | — | — |
| #C46$^{NA}$ | 12903 | 4322 | 1173 | 289 | 48 | — | — | — | — | — |
| #C26$^{NA}$ | 14631 | 3924 | 818 | 166 | 7 | — | — | — | — | — |
| #17 | 17532 | 8788 | 4384 | 2146 | 562 | 14026 | 7030 | 3507 | 1717 | 450 |
| #C2 | 25284 | 11232 | 3337 | 1227 | 164 | 20227 | 8986 | 2670 | 982 | 131 |
| #16 | 27653 | 13182 | 5708 | 2401 | 417 | 22122 | 10545 | 4566 | 1921 | 334 |
| #14 | 39203 | 19502 | 6476 | 2222 | 270 | 31362 | 15602 | 5181 | 1777 | 216 |
| #C3 | 44211 | 19353 | 5739 | 1972 | 430 | 35369 | 15482 | 4592 | 1577 | 344 |
| #C47 | 58775 | 29155 | 11501 | 4200 | 858 | 47020 | 23356 | 9201 | 3360 | 686 |
| NSF1 | 62359 | 28524 | 13591 | 6599 | 1648 | 49887 | 22820 | 10873 | 5279 | 1319 |
| #15 | 62583 | 27826 | 8138 | 2571 | 324 | 50067 | 22260 | 6510 | 2056 | 259 |
| #C46$^{CO}$ | 79585 | 33443 | 10047 | 3183 | 344 | 63668 | 26754 | 8038 | 2547 | 275 |
| #C42 | 93588 | 40008 | 13596 | 4162 | 414 | 74871 | 32007 | 10877 | 3330 | 331 |
| #C49 | 94271 | 43860 | 18244 | 7505 | 1567 | 75417 | 35088 | 14595 | 6004 | 1254 |
| #C48 | 95380 | 45839 | 17874 | 7041 | 1450 | 76304 | 36671 | 14300 | 5633 | 1160 |
| #C36 | 97598 | 41681 | 10992 | 2532 | 304 | 78079 | 33345 | 8793 | 2026 | 243 |
| #C22 | 104245 | 42647 | 10779 | 2220 | 98 | 83396 | 34118 | 8623 | 1776 | 78 |
| #C1 | 106066 | 47905 | 14656 | 4114 | 490 | 84853 | 38324 | 11725 | 3291 | 392 |
| #C44 | 113036 | 46921 | 16587 | 4981 | 432 | 90429 | 37537 | 13270 | 3985 | 345 |
| #C36$^{CO}$ | 115013 | 55385 | 16819 | 4470 | 605 | 92010 | 44308 | 13455 | 3576 | 484 |
| #C46 | 116504 | 58210 | 15157 | 2835 | 158 | 93203 | 46568 | 12126 | 2268 | 126 |
| #C10 | 122810 | 53552 | 22814 | 10040 | 1876 | 98248 | 42842 | 18252 | 8032 | 1501 |
| #C29 | 125773 | 56542 | 18978 | 6233 | 960 | 100618 | 45233 | 15182 | 4986 | 768 |
| #C43 | 133120 | 59011 | 19937 | 5479 | 529 | 106496 | 47208 | 15950 | 4383 | 423 |

TABLE 8-continued

Sub-visible particle content after drop test

| | Total Particles (counts/mL) | | | | | Total Particles (counts/container) | | | | |
|---|---|---|---|---|---|---|---|---|---|---|
| Formula | All | ≥2 uM | ≥5 uM | ≥10 uM | ≥25 uM | All | ≥2 uM | ≥5 uM | ≥10 uM | ≥25 uM |
| #C9 | 133521 | 59593 | 26218 | 12097 | 2278 | 106817 | 47674 | 20975 | 9677 | 1823 |
| #C26 | 136982 | 54196 | 12976 | 2252 | 104 | 109586 | 43357 | 10381 | 1802 | 83 |
| #C21 | 138707 | 46670 | 13639 | 4310 | 624 | 110966 | 37336 | 10911 | 3448 | 499 |
| #C15 | 149015 | 61627 | 19025 | 5861 | 699 | 119212 | 49302 | 15220 | 4689 | 559 |
| #C41 | 150938 | 69151 | 24231 | 7587 | 793 | 120750 | 55321 | 19385 | 6069 | 634 |
| #C6 | 151993 | 48475 | 13140 | 3376 | 396 | 121594 | 38780 | 10512 | 2701 | 317 |
| #C23 | 157762 | 69529 | 20000 | 5327 | 629 | 126209 | 55624 | 16000 | 4261 | 504 |
| #C26$^{CO}$ | 164986 | 54667 | 15882 | 4769 | 656 | 131989 | 43734 | 12705 | 3815 | 525 |
| #C35 | 171152 | 66031 | 22186 | 7437 | 1095 | 136922 | 52825 | 17749 | 5950 | 876 |
| #C37 | 175637 | 85387 | 31884 | 10940 | 1628 | 140509 | 68310 | 25508 | 8752 | 1302 |
| #C12 | 180126 | 75126 | 25908 | 8875 | 1075 | 144101 | 60101 | 20726 | 7100 | 860 |
| #C4 | 183520 | 84387 | 34302 | 13862 | 2104 | 146816 | 67510 | 27442 | 11090 | 1684 |
| #C39 | 185166 | 84072 | 35284 | 14686 | 3134 | 148133 | 67257 | 28227 | 11748 | 2507 |
| #C36$^{R}$ | 188174 | 83974 | 25376 | 6919 | 651 | 150539 | 67179 | 20301 | 5535 | 521 |
| #C17 | 188363 | 67378 | 20339 | 6992 | 1021 | 150690 | 53903 | 16271 | 5594 | 816 |
| #C8 | 189720 | 77152 | 28960 | 10844 | 1437 | 151776 | 61721 | 23168 | 8676 | 1150 |
| #C13 | 190217 | 88514 | 36007 | 14172 | 2250 | 152174 | 70812 | 28806 | 11337 | 1800 |
| #C40 | 190666 | 86822 | 26751 | 7218 | 671 | 152533 | 69458 | 21401 | 5774 | 537 |
| #C38 | 196746 | 79163 | 21051 | 5205 | 412 | 157409 | 63331 | 16841 | 4164 | 330 |
| #C33 | 198695 | 82887 | 24930 | 6989 | 823 | 158956 | 66310 | 19944 | 5591 | 658 |
| #C20 | 204832 | 71497 | 20886 | 7088 | 1016 | 163866 | 57198 | 16709 | 5671 | 813 |
| #C11 | 214769 | 92430 | 33418 | 13659 | 2718 | 171815 | 73944 | 26734 | 10927 | 2174 |
| #C27 | 225266 | 81696 | 16350 | 2472 | 187 | 180213 | 65357 | 13080 | 1978 | 149 |
| #C5 | 260811 | 108172 | 40793 | 14745 | 2000 | 208649 | 86537 | 32634 | 11796 | 1600 |
| #C31 | 261254 | 100296 | 26275 | 6618 | 761 | 209003 | 80237 | 21020 | 5294 | 609 |
| #C34 | 266052 | 94864 | 24753 | 5069 | 423 | 212842 | 75891 | 19802 | 4055 | 339 |
| #24 | 268681 | 95903 | 21360 | 3368 | 236 | 214945 | 76722 | 17088 | 2694 | 189 |
| #C28 | 274738 | 95918 | 21115 | 3089 | 221 | 219791 | 76734 | 16892 | 2471 | 177 |
| #C19 | 288419 | 108722 | 32463 | 10855 | 1526 | 230735 | 86978 | 25970 | 8684 | 1221 |
| #C32 | 299420 | 128648 | 36345 | 8504 | 917 | 239536 | 102918 | 29076 | 6803 | 734 |
| #C30 | 348504 | 133911 | 36305 | 9802 | 1351 | 278804 | 107129 | 29044 | 7841 | 1081 |

$^{ND}$denotes a "no drop" control test
$^{CO}$denotes that the air gap in the pre-filled syringe was replaced with $CO_2$
$^{NA}$denotes that the air gap in the pre-filled syringe was removed
$^{R}$denotes a repeat test Results Formulations containing HPβCD, PEG300 and combinations thereof resulted in the fewest total sub-visible particles. Specifically, Formulation #17, which contains 2% PEG300, contained the fewest total sub-visible particles followed by Formulation #C2, which contains 1% PEG300 and 1% HPβCD and then Formulation #16, which contains 1% PEG 300, and then Formulation #14, which contains 1% HPβCD.

Example 6. HPβCD Enhances Colloidal Stability of Adalimumab

Figure 3:
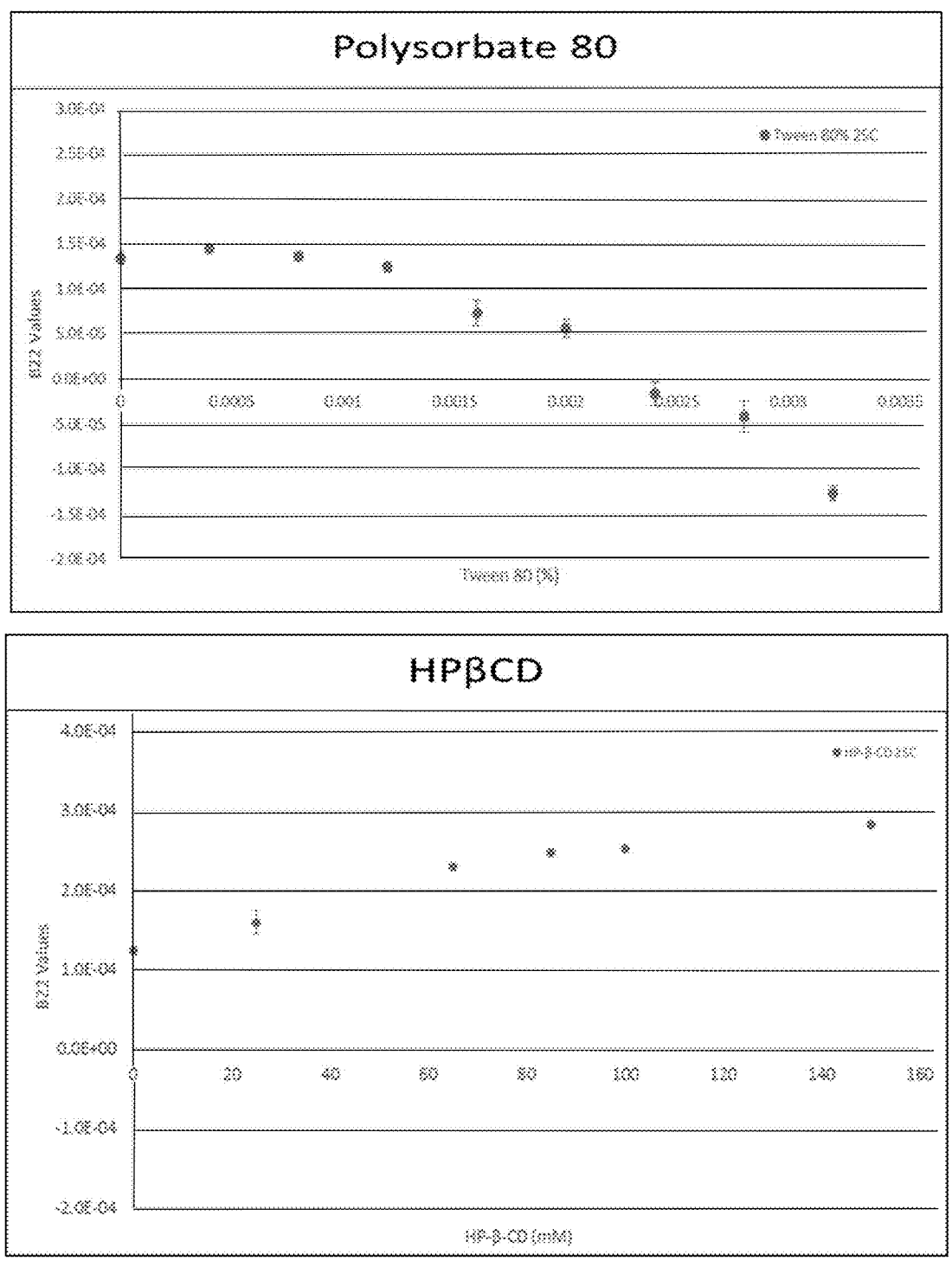
FIG. 3. B22, the second virial coefficient, calculations from self-interaction chromatograms (SIC) of adalimumab formulations for HPβCD and the surfactant polysorbate 80.

The ability to affect colloidal stability of adalimumab was evaluated for HPβCD and the surfactant polysorbate 80. To assess colloidal stability, B22, the second virial coefficient, was calculated from self-interaction chromatograms (SIC) of adalimumab formulations. The results are presented in FIG. 3.

Surprisingly, increasing the concentration of polysorbate 80 and HPβCD have opposite effects on the colloidal stability of adalimumab. Polysorbate 80 increased attractive interactions (i.e. reduced colloidal stability) while HPβCD reduced attractive interactions (i.e. increased colloidal stability). The stabilizing effects of HPβCD was seen at concentrations from about 25 mM to about 150 mM. As a result, proteins in formulations with HPβCD are stable. Increasing colloidal stability is known to reduce aggregation and reduce viscosity of formulations. Improved colloidal stability may also result in reduced surface tension.

Example 7. Stability of Adalimumab formulations with HPβCD

The stability of various adalimumab formulations that contain HPβCD and are free of surfactant was evaluated. Formulations contain adalimumab at various concentrations (e.g. about 50 mg/mL and about 100 mg/mL), and the presence or absence of a buffer.

| | Adalimumab formulations with HPβCD and those without (controls) include: |
|---|---|
| A | 50 mg/mL adaliumamb, 20 mM His, 25 mM NaCl, 100 mM Gly, 70 mM HPβCD, pH 5.2 |
| B | 50 mg/mL adalimuamb, 20 mM His, 25 mM NaCl, 180 mM Gly, 70 mM HPβCD, pH 5.2 |
| C | 50 mg/mL adalimuamb, 20 mM His, 25 mM NaCl, 140 mM Gly, 65 mM HPβCD, pH 5.2 |
| D | 50 mg/mL adalimuamb, 35 mM NaCl, 140 mM Gly, 65 mM HPβCD, pH 5.2 |
| E (Humira 50 mg/mL) | 50 mg/mL adalimuamb, 1.3 mg/mL citric acid monohydrate, 1.525 mg/mL dibasic sodium phosphate dihyrdate, 12 mg/mL mannitol, 0.8625 mg/mL monobasic sodium phosphate dihyrdate, 1.0 mg/mL polysorbate 80, 6.1625 mg/mL sodium chloride and 0.3 mg/mL sodium citrate, pH 5.2 |
| F | 100 mg/mL adalimuamb, 10 mM His, 25 mM NaCl, 90 mM Gly, 65 mM HPβCD, pH 5.2 |
| G | 100 mg/mL adalimuamb, 40 mM NaCl, 90 mM Gly, 65 mM HPβCD, pH 5.2 |

-continued

Adalimumab formulations with HPβCD and those without (controls) include:

| | |
|---|---|
| H (Humira 100 mg/mL) | 100 mg/mL adalimuamb, 42 mg/mL Mannitol, 1.0 mg/mL PS80, pH 5.2 |

Characterization of HPβCD Formulations

Surfactant free adalimumab formulations with HPβCD characterized and compared to Humira formulations in the tables below.

| Form No | Viscosity (cP) | Tonicity (mOsm/Kg) | Conductivity (mS/cm) |
|---|---|---|---|
| A | NA | 309 | 3.5 |
| B | NA | 436 | 3.8 |
| C | 2.0 | 355 | 3.7 |
| D | 2.0 | 354 | 3.5 |
| E | 1.4 | 334 | 11.9 |
| F | 3.8 | 335 | 3.3 |
| G | 3.8 | 334 | 3.2 |
| H | 3.1 | 307 | 1.0 |

The results in the table above demonstrate the adalimumab formulations with HPβCD that do not contain a surfactant have viscosities and tonicity that is comparable Humira formulations with the same concentration of adalimumab. With the exception of formulation B, all the tonicity of all formulations is between about 250 and about 350 mOsm/Kg indicating they are about isotonic. The tonicity of formulations that contain salt, like formulation B, can be readily adjusted by reducing the amount of salt to reduce tonicity or adding salt to increase to increase tonicity. The conductivity of adalimumab formulations F and G is greater than 3.0 as a result of the ionic excipients (e.g. buffer, salt) while formulation H does not contain any ionic excipients. Formulations with HPβCD that are free or substantially free of surfactant are suitable for administration to a subject.

Stability of HPβCD Formulations

The stability of protein formulations with HPβCD that are free or substantially free of surfactant was evaluated over time. Evaluations include, but are not limited to: pH, protein concentration, size exclusion chromatography, cation exchange chromatography, CE-SDS (reducing and non-reducing), potency, clarity (NTU), visual inspection (clarity, turbidity, particles), and sub-visible particles. Storage temperature and times may include: −40° C. for 1, 3, 6, and 12 months; 2-8° C. for 1, 3, 6, and 12 months; and 25° C. for 2 weeks, 1 month, 3 months, and 6 months; and 40° C. for 1, 2, and 4 weeks.

TABLE m

Adalimumab formulation A

| Temp (° C.) | Time (month) | pH | Conc (mg/mL) | Visual | Particulate per container ≥10 μm | ≥25 μm |
|---|---|---|---|---|---|---|
| 5 | 0 | 5.4 | 47.3 | Clear | 405 | 75 |
| | 1 | 5.4 | 46.8 | Clear | 297 | 22 |
| 25 | 0 | 5.4 | 47.3 | Clear | 405 | 75 |
| | 0.5 | NA | NA | Clear | 5 | 0 |
| | 1 | 5.4 | 47.6 | Clear | 265 | 15 |
| 40 | 0 | 5.4 | 47.3 | Clear | 405 | 75 |
| | 0.25 | NA | NA | Clear | 178 | 61 |
| | 0.5 | NA | NA | Clear | 109 | 30 |
| | 1 | 5.4 | 50.3 | Visible Particle | 884 | 72 |

TABLE n

Adalimumab formulation A

| Temp (°C) | Time (month) | SEC (%) Main | Aggregate | Post Peak | CEX (%) Main | Acidic |
|---|---|---|---|---|---|---|
| 5 | 0 | 99.7 | 0.1 | 0.2 | 79.8 | 13.2 |
| | 1 | 99.7 | 0.1 | 0.2 | 79.7 | 13.5 |
| 25 | 0 | 99.7 | 0.1 | 0.2 | 79.8 | 13.2 |
| | 0.5 | 99.6 | 0.1 | 0.3 | 78.6 | 14.2 |
| | 1 | 99.4 | 0.1 | 0.4 | 77.0 | 15.6 |
| 40 | 0 | 99.7 | 0.1 | 0.2 | 79.8 | 13.2 |
| | 0.25 | 99.3 | 0.1 | 0.5 | 73.7 | 18.1 |
| | 0.5 | 98.9 | 0.2 | 1.0 | 67.3 | 23.4 |
| | 1 | 97.9 | 0.3 | 1.7 | 55.7 | 33.5 |

TABLE x

Adalimumab formulation B

| Temp (° C.) | Time (month) | pH | Conc (mg/mL) | Particulate per container ≥10 μm | ≥25 μm |
|---|---|---|---|---|---|
| 5 | 0 | 5.5 | 48.6 | 801 | 64 |
| | 1 | 5.5 | 48.6 | NA | NA |
| | 2 | 5.5 | 48.5 | 105 | 10 |
| 25 | 0 | 5.5 | 48.6 | 801 | 64 |
| | 0.5 | 5.5 | 47.9 | NA | NA |
| | 1 | 5.5 | 48.4 | NA | NA |
| | 2 | 5.5 | 48.2 | | |
| 40 | 0 | 5.5 | 48.6 | 801 | 64 |
| | 0.25 | 5.5 | 48.9 | NA | NA |
| | 0.5 | 5.5 | 48.4 | NA | NA |

TABLE y

Adalimumab formulation B

| Temp (° C.) | Time (month) | SEC (%) Main | Aggregate | Post Peak | CEX (%) Main | Acidic |
|---|---|---|---|---|---|---|
| 5 | 0 | 99.1 | 0.7 | 0.1 | 81.8 | 12.2 |
| | 1 | 99.1 | 0.7 | 0.2 | 81.4 | 12.6 |
| | 2 | 99.0 | 0.8 | 0.1 | 81.5 | 12.6 |
| 25 | 0 | 99.1 | 0.7 | 0.1 | 81.8 | 12.2 |
| | 0.5 | 99.0 | 0.7 | 0.3 | 80.2 | 13.4 |
| | 1 | 99.0 | 0.7 | 0.3 | 78.7 | 14.7 |
| | 2 | 98.4 | 0.9 | 0.7 | 75.5 | 17.5 |
| 40 | 0 | 99.1 | 0.7 | 0.1 | 81.8 | 12.2 |
| | 0.25 | 99.1 | 0.7 | 0.3 | 75.3 | 17.2 |
| | 0.5 | 98.9 | 0.7 | 0.5 | 69.3 | 22.1 |

The results in the tables above demonstrate the adalimumab formulations with HPβCD that do not contain a surfactant are stable. [00447] Particle counts for particles ≥10 μm and ≥25 μm were low in formulation A, but raised in formulation B. However, SEC analysis shows the formulations maintained greater than 97% main peak percentage, less than 3% aggregates, and less than 3% post peak species, whether stored at 5° C., 25° C. or 40° C. CEX analysis likewise showed that the formulations were stable.

The results above demonstrate that a protein formulation that contain HPβCD and that are free or substantially free of surfactant are stable. This is surprising since many protein formulation, including the adalimumab formulations for Humira® and Amjevita™, contain a surfactant. These results show for the first time that protein formulations can be stabilized with HPβCD without the need for excipients such as surfactants, polyols, sugars, and buffers.

What is claimed is:

1. A stable adalimumab composition comprising:
   (i) about 25 mg/mL to about 120 mg/mL adalimumab or a biosimilar thereof;
   (ii) about 5 mM to about 50 mM of a buffer;
   (iii) about 10 mM to about 300 mM of an amino acid; and
   (iv) at least one excipient selected from the group consisting of:
      about 10 mM to about 150 mM of a cyclodextrin;
      about 0.1% w/v to about 5% w/v of a cellulose derivative;
      about 1% w/v to about 2% w/v of a polyethylene glycol; and
   a salt present at a concentration of less than 50 mM,
   wherein the composition is free of surfactant, and the composition is stable at a temperature of 25° C. for two weeks or at a temperature of 40° C. for one week.

2. The composition of claim 1, wherein the composition is free or substantially free of polyol.

3. The composition of claim 1, wherein the cyclodextrin is an alpha cyclodextrin, beta cyclodextrin, gamma cyclodextrin, or combinations thereof.

4. The composition of claim 3, wherein the alpha cyclodextrin, beta cyclodextrin, or gamma cyclodextrin is a derivatized cyclodextrin.

5. The composition of claim 4, wherein the derivatized beta cyclodextrin comprises: methyl-beta-cyclodextrins ("MβCD"), randomly methylated-beta-cyclodextrin ("RMβCD"), Sulfobutylether-beta-cyclodextrins ("SBEβCD"), or hydroxypropyl-beta-cyclodextrins ("HPβCD").

6. The composition of claim 5, wherein the derivatized beta cyclodextrin is HPβCD.

7. The composition of claim 6, wherein HPβCD is present at a concentration of about 25 mM to about 100 mM.

8. The composition of claim 1, wherein the at least one excipient comprises at least two polyethylene glycols.

9. The composition of claim 8, wherein each of the at least two polyethylene glycols have a molecular weight from 200 daltons to 20 kilodaltons.

10. The composition of claim 1, wherein adalimumab or a biosimilar thereof is present at a concentration of about 50 mg/mL to about 100 mg/mL.

11. The composition of claim 1, wherein the composition has a pH of about 4 to about 5.

12. The composition of claim 1, wherein the composition exhibits long term stability.

13. The composition of claim 1, wherein the composition is a pharmaceutical composition.

14. The composition of claim 13, wherein the composition is a liquid composition.

15. The composition of claim 14, wherein the liquid composition is suitable for administration to a subject.

16. The composition of claim 1, wherein the composition is isotonic or has an osmolality of about 180 to about 420 mOsM.

17. The composition of claim 1, wherein the composition has a conductivity of greater than 2.5 mS/cm.

18. The composition of claim 1, wherein the composition comprises a salt at a concentration of less than 50 mM.

19. The composition of claim 1, wherein the buffer comprises phosphate, pyrophosphate, citrate, acetate, glutamate, gluconate, histidine, succinate, adipate, maleate, tartrate, or combinations thereof.

20. The composition of claim 19, wherein the buffer is histidine.

21. The composition of claim 20, wherein the histidine buffer is present at a concentration of about 10 mM to about 30 mM.

22. The composition of claim 1, further comprising a polyol.

23. The composition of claim 18, wherein the salt comprises NaCl, KCl, $Na_2SO_4$, $MgCl_2$, $CaCl_2$, or adipate.

24. The composition of claim 23, wherein the salt is present at a concentration of less than 28 mM.

25. The composition of claim 1, wherein the amino acid is selected from the group consisting of histidine, glycine, methionine, serine, proline, and arginine, and combinations thereof.

26. A stable adalimumab composition comprising:
   (i) about 25 mg/mL to about 120 mg/mL adalimumab or a biosimilar thereof;
   (ii) about 5 mM to about 50 mM of a buffer;
   (iii) about 10 mM to about 300 mM of an amino acid; and
   (iv) at least one excipient selected from the group consisting of:
      about 10 mM to about 150 mM of a cyclodextrin;
      about 0.1% w/v to about 5% w/v of a cellulose derivative;
      about 1% w/v to about 2% w/v of a polyethylene glycol; and
   a salt present at a concentration of less than 50 mM,
   wherein the composition is free of surfactant; and the composition has stability comparable to or better than a composition comprising adalimumab or a biosimilar thereof and surfactant, and the composition is stable at a temperature of 25° C. for two weeks or at a temperature of 40° C. for one week.

27. A stable pharmaceutical composition comprising:
   (i) about 25 mg/mL to about 120 mg/mL adalimumab or a biosimilar thereof;
   (ii) about 5 mM to about 50 mM of a buffer;
   (iii) about 10 mM to about 300 mM of an amino acid; and
   (iv) about 10 mM to about 150 mM HPβCD;
   wherein the composition is free of surfactant, and the composition is stable at a temperature of 25° C. for two weeks or at a temperature of 40° C. for one week.

28. The composition of claim 27, wherein the composition is free or substantially free of polyol.

29. The composition of claim 27, wherein the adalimumab or biosimilar thereof is present at a concentration of about 50 mg/mL to about 100 mg/mL.

30. The composition of claim 27, wherein HPβCD is present at a concentration of about 25 mM to about 100 mM.

31. The composition of claim 27, wherein the composition has a pH of about 5 to about 6.

32. The composition of claim 27, wherein the composition exhibits long term stability.

33. The composition of claim 27, wherein the composition is suitable for administration to a subject.

34. The composition of claim 27, wherein the composition is isotonic or has an osmolality of about 180 to about 420 mOsM.

35. The composition of claim 27, wherein the composition has a conductivity of greater than 2.5 mS/cm.

36. The composition of claim 27, wherein the composition further comprises a salt at a concentration of less than 50 mM.

37. The composition of claim 27, wherein the buffer comprises phosphate, pyrophosphate, citrate, acetate, glutamate, gluconate, histidine, succinate, adipate, maleate, tartrate, or combinations thereof.

38. The composition of claim 37, wherein the buffer is histidine.

39. The composition of claim 38, wherein the histidine buffer is present at a concentration of about 10 mM to about 30 mM.

40. The composition of claim 27, wherein the composition is (a) free of citrate buffer; or (b) free of phosphate buffer; or (c) free of a buffer composition comprising citrate buffer and phosphate buffer.

41. The composition of claim 27, further comprising a polyol.

42. The composition of claim 36, wherein the salt comprises NaCl, KCl, Na$_2$SO$_4$, MgCl$_2$, CaCl$_2$, or adipate.

43. The composition of claim 42, wherein the salt is present at a concentration of less than 28 mM.

44. The composition of claim 27, wherein the amino acid is selected from the group consisting of histidine, glycine, methionine, serine, proline, and arginine, and combinations thereof.

* * * * *

UNITED STATES PATENT AND TRADEMARK OFFICE
CERTIFICATE OF CORRECTION

| | |
|---|---|
| PATENT NO. | : 11,583,584 B1 |
| APPLICATION NO. | : 15/337845 |
| DATED | : February 21, 2023 |
| INVENTOR(S) | : Jun Liu, Mark Manning and Isaias Prado |

It is certified that error appears in the above-identified patent and that said Letters Patent is hereby corrected as shown below:

On the Title Page

In the title and in the Specification, Column 1, Line 1, please delete "PROTEIN" and insert -- ADALIMUMAB --.

Signed and Sealed this
Eleventh Day of April, 2023

Katherine Kelly Vidal
Director of the United States Patent and Trademark Office